United States Patent
Kushki et al.

(10) Patent No.: US 9,844,332 B2
(45) Date of Patent: Dec. 19, 2017

(54) ANXIETY METER

(71) Applicant: Holland Bloorview Kids Rehabilitation Hospital, Toronto (CA)

(72) Inventors: Azadeh Kushki, Toronto (CA); Evdokia Anagnostou, Toronto (CA)

(73) Assignee: Holland Bloorview Kids Rehabilitation Hospital, Toronto (CA)

( * ) Notice: Subject to any disclaimer, the term of this patent is extended or adjusted under 35 U.S.C. 154(b) by 247 days.

(21) Appl. No.: 14/755,084

(22) Filed: Jun. 30, 2015

(65) Prior Publication Data

US 2016/0000365 A1 Jan. 7, 2016

Related U.S. Application Data

(60) Provisional application No. 62/021,272, filed on Jul. 7, 2014.

(51) Int. Cl.
| | |
|---|---|
| A61B 5/02 | (2006.01) |
| A61B 5/16 | (2006.01) |
| A61B 5/024 | (2006.01) |
| A61B 5/00 | (2006.01) |
| A61B 5/053 | (2006.01) |

(52) U.S. Cl.
CPC .............. *A61B 5/165* (2013.01); *A61B 5/024* (2013.01); *A61B 5/725* (2013.01); *A61B 5/0533* (2013.01); *A61B 5/6802* (2013.01); *A61B 5/6898* (2013.01); *A61B 5/742* (2013.01)

(58) Field of Classification Search
CPC .......... A61B 5/024; A61B 5/165; A61B 5/725
See application file for complete search history.

(56) References Cited

U.S. PATENT DOCUMENTS

| | | | |
|---|---|---|---|
| 8,700,009 B2* | 4/2014 | Quy | H04W 4/00 |
| | | | 455/414.1 |
| 2011/0245633 A1* | 10/2011 | Goldberg | A61B 5/681 |
| | | | 600/301 |

OTHER PUBLICATIONS

Sinopoli et al. "Kalman Filtering with Intermittent Observations" IEEE Transactions on Automatic Control, vol. 49, No. 9, Sep. 2004.*
D. H. Barlow, "Unraveling the Mysteries of Anxiety and Its Disorders From the Perspective of Emotion Theory." American Psychologist, vol. 55, No. 11, pp. 1247-1263, 2000.
J. Zhai and A. Barreto, "Stress Detection in Computer Users Based on Digital Signal Processing of Noninvasive Physiological Variables," in Engineering in Medicine and Biology Society, 2006. EMBS'06. 28th Annual International Conference of the IEEE. IEEE, 2006, pp. 1355-1358.
J. A. Healey and R. W. Picard, "Detecting Stress During Real-World Driving Tasks Using Physiological Sensors," Intelligent Transportation Systems, IEEE Transactions on, vol. 6, No. 2, pp. 156-166, 2005.
A. de Santos Sierra, C. S. A' vila, J. Guerra Casanova, and G. B. del Pozo, "A Stress-Detection System Based on Physiological Signals and Fuzzy Logic," Industrial Electronics, IEEE Transactions on, vol. 58, No. 10, pp. 4857-4865, 2011.

(Continued)

*Primary Examiner* — Christian Jang
(74) *Attorney, Agent, or Firm* — Ridout & Maybee LLP

(57) ABSTRACT

Methods and systems for detection of anxiety using physiological signals. The detection of anxiety may take place in real-time and in a naturalistic setting. A modified Kalman filter may be used.

14 Claims, 13 Drawing Sheets

(56) References Cited

OTHER PUBLICATIONS

M. J. Skinner and P. A. Simpson, "Workload Issues in Military Tactical Airlift," The International Journal of Aviation Psychology, vol. 12, No. 1, pp. 79-93, 2002.
F.T. Sun, C. Kuo, H.-T. Cheng, S. Buthpitiya, P. Collins, and M. Griss, "Activity-aware Mental Stress Detection Using Physiological Sensors," in Mobile Computing, Applications, and Services. Springer, 2012, pp. 211-230.
A. Kushki, E. Drumm, M. P. Mobarak, N. Tanel, A. Dupuis, T. Chau, and E. Anagnostou, "Investigating the Autonomic Nervous System Response to Anxiety in Children with Autism Spectrum Disorders," PLoS one, vol. 8, No. 4, p. e59730, 2013.
P. J. Lang, "Fear Reduction and Fear Behavior: Problems in Treating a Construct." in Research in Psychotherapy Conference, 3rd, May-Jun. 1966, Chicago, IL, US. American Psychological Association, 1968, pp. 90-102.
D. Robertson, I. Biaggioni, G. Burnstock, P. A. Low, and J. F. Paton, "Primer on the Autonomic Nervous System". Access Online via Elsevier, 2011.
A. Camm, M. Malik, J. Bigger, G. Breithardt, S. Cerutti, R. Cohen, P. Coumel, E. Fallen, H. Kennedy, R. Kleiger et al., "Heart Rate Variability: Standards of Measurement, Physiological Interpretation and Clinical Use. Task Force of the European Society of Cardiology and the North American Society of Pacing and Electrophysiology," Circulation, vol. 93, No. 5, pp. 1043-1065, 1996.
Y. Bar-Shalm, X. R. Li, and T. Kirubarajan, "Estimation with Applications to Tracking and Navigation: Theory Algorithms and Software". John Wiley & Sons, 2004.
O. L. do Valle Costa, M. D. Fragoso, and R. P. Marques, "Discrete-Time Markov Jump Linear Systems". Springer, 2006.
D. E. Gustafson, A. S. Willsky, I.-Y. Wang, M. C. Lancaster, and J. H. Triebwasser, "ECG/VCG Rhythm Diagnosis Using Statistical Signal Analysis-I. Identification of Persistent Rhythms," Biomedical Engineering, IEEE Transactions on, No. 4, pp. 344-353, 1978.
D. F. Sittig and K.-H. Cheung, "A Parallel Implementation of a Multi-State Kalman Filtering Algorithm to Detect ECG Arrhythmias," International journal of clinical monitoring and computing, vol. 9, No. 1, pp. 13-22, 1992.
J McNames and M. Aboy, "Statistical Modeling of Cardiovascular Signals and Parameter Estimation Based on the Extended Kalman Filter," Biomedical Engineering, IEEE Transactions on, vol. 55, No. 1, pp. 119-129, 2008.
B. Sinopoli, L. Schenato, M. Franceschetti, K. Poolla, M. I. Jordan, and S. S. Sastry, "Kalman Filtering With Intermittent Observations," Automatic Control, IEEE Transactions on, vol. 49, No. 9, pp. 1453-1464, 2004.
S.White, D. Oswald, T. Ollendick, and L. Scahill, "Anxiety in Children and Adolescents with Autism Spectrum Disorders," Clinical Psychology Review, vol. 29, No. 3, pp. 216-229, 2009.
B. MacNeil, V. Lopes, and P. Minnes, "Anxiety in Children and Adolescents with Autism Spectrum Disorders," Research in Autism Spectrum Disorders, vol. 3, No. 1, pp. 1-21, 2009.
J. Reaven, "Children with High-Functioning Autism Spectrum Disorders and Co-occurring Anxiety Symptoms: Implications for Assessment and Treatment," Journal for Specialists in Pediatric Nursing, vol. 14, No. 3, pp. 192-199, 2009.
D. Sukhodolsky, L. Scahill, K. Gadow, L. Arnold, M. Aman, C. McDougle, J. McCracken, E. Tierney, S. Williams White, L. Lecavalier et al., "Parent-Rated Anxiety Symptoms in Children with Pervasive Developmental Disorders: Frequency and Association with Core Autism Symptoms and Cognitive Functioning," Journal of Abnormal Child Psychology, vol. 36, No. 1, pp. 117-128, 2008.
A. Blakeley-Smith, J. Reaven, K. Ridge, and S. Hepburn, "Parent-Child Agreement of Anxiety Symptoms in Youth with Autism Spectrum Disorders," Research in Autism Spectrum Disorders, vol. 6, No. 2, pp. 707-716, 2012.
A. Kushki, J. Brian, T. Dupuis A, and A. E, "Functional Autonomic Nervous System Profile in Children with Autism Spectrum Disorder," Molecular Autism, Submitted 2014.
C. Lord, S. Risi, L. Lambrecht, E. Cook, B. Leventhal, P. DiLavore, A. Pickles, and M. Rutter, "The Autism Diagnostic Observation Schedule—Generic: A Standard Measure of Social and communication Deficits Associated with the Spectrum of Autism," Journal of autism and developmental disorders, vol. 30, No. 3, pp. 205-223, 2000.
C. Lord, M. Rutter, and A. Le Couteur, "Autism Diagnostic Interview—Revised: A Revised Version of a Diagnostic Interview for Caregivers of Individuals with Possible Pervasive Developmental Disorders," Journal of autism and developmental disorders, vol. 24, No. 5, pp. 659-685, 1994.
C. Ebesutani, A. Bernstein, B. J. Nakamura, B. F. Chorpita, and J. R. Weisz, "A Psychometric Analysis of the Revised Child Anxiety and Depression Scale—Parent Version in a Clinical Sample," Journal of abnormal child psychology, vol. 38, No. 2, pp. 249-260, 2010.
J. Stroop, "Studies of Interference in Serial Verbal Reactions." Journal of Experimental Psychology, vol. 18, No. 6, pp. 643-662, 1935.
M. Fechir, M. Gamer, I. Blasius, T. Bauermann, M. Breimhorst, P. Schlindwein, T. Schlereth, and F. Birklein, "Functional Imaging of Sympathetic Activation During Mental Stress," Neuroimage, vol. 50, No. 2, pp. 847-854, 2010.
Y Boutcher and S. Boutcher, "Cardiovascular Response to Stroop: Effect of Verbal Response and Task Difficulty," Biological psychology, vol. 73, No. 3, pp. 235-241, 2006.
L. W. Carlile et al., "Special Reports: Heart Rate as an Index of Speech Anxiety." Speech Monographs, vol. 38, No. 1, pp. 65-69, 1971.
M. J. Beatty and R. R. Behnke, "Effects of Public Speaking Trait Anxiety and Intensity of Speaking Task on Heart Rate During Performance," Human Communication Research, vol. 18, No. 2, pp. 147-176, 1991.
M. Pö rhö lä, "Arousal Styles During Public Speaking," Communication Education, vol. 51, No. 4, pp. 420-438, 2002.
L. Jansen, C. Gispen-De Wied, R. Van Der Gaag, and H. Van Engeland, "Differentiation Between Autism and Multiple Complex Developmental Disorder in Response to Psychosocial Stress," Neuropsychopharmacology, vol. 28, No. 3, pp. 582-590, 2003.
T. Levine, D. Dhossche, C. Ross, L. Stoppelbein, J. Charles, C. Harrison, H. Britt, A. Estes, V. Hus, L. Elder et al., "Physiologic Arousal to Social Stress in Children with Autism Spectrum Disorders: A Pilot Study," Research in Autism Spectrum Disorders, vol. 6, No. 1, pp. 177-183, 2012.
J. Pan and W. J. Tompkins, "A Real-Time QRS Detection Algorithm," Biomedical Engineering, IEEE Transactions on, No. 3, pp. 230-236, 1985.
P. S. Hamilton and W. J. Tompkins, "Quantitative Investigation of QRS Detection Rules Using the MIT/BIH Arrhythmia Database," Biomedical Engineering, IEEE Transactions on, No. 12, pp. 1157-1165, 1986.
Lang R, Regester A, Lauderdale S, Ashbaugh K, Haring A (2010) "Treatment of Anxiety in Autism Spectrum Disorders using Cognitive Behaviour Therapy: A Systematic Review". Developmental Neurorehabilitation 13: 53-63.
Gillott A, Furniss F, Walter A (2001) "Anxiety in High-Functioning Children with Autism". Autism 5: 277-286.
White S, Roberson-Nay R (2009) "Anxiety, Social Deficits, and Loneliness in Youth with Autism Spectrum Disorders". Journal of autism and developmental disorders 39:1006-1013.
Farrugia S, Hudson J (2006) "Anxiety in Adolescents with Asperger Syndrome: Negative Thoughts, Behavioral Problems, and Life Interference". Focus on Autism and Other Developmental Disabilities 21: 25-35.
Kim J, Szatmari P, Bryson S, Streiner D, Wilson F (2000) "The Prevalence of Anxiety and Mood Problems Among Children with Autism and Asperger Syndrome". Autism 4: 117-132.
Helverschou S, Martinsen H (2011) "Anxiety in People Diagnosed with Autism and Intellectual Disability: Recognition and Phenomenology". Research in Autism Spectrum Disorders 5: 377-387.
Amaral D, Corbett B (2003) "The Amygdala, Autism and Anxiety". In: Novartis Foundation symposium. vol. 251, p. 177.

(56) References Cited

OTHER PUBLICATIONS

Franchini KG, Cowley AW (2011) "Autonomic Control of Cardiac Function". In: Robertson D, Biaggioni I, Burnstock G, Low P, Paton J, editors, Primer on the autonomic nervous system, Academic Press. 134-138.

Dawson M, Schell A, Filion D (2000) "The Electrodermal System". In: Cacioppo J, Tassinary LG, Berntson GG, editors, Handbook of psychophysiology, (Cam-bridge University Press). 200-223.

Vetrugno R, Liguori R, Cortelli P, Montagna P (2003) "Sympathetic Skin Response". Clinical autonomic research 13: 256-270.

Franchini KG, Cowley AW (2011) "Neurogenic Control of Blood Vessels". In: Robertson D, Biaggioni I, Burnstock G, Low P, Paton J, editors, Primer on the autonomic nervous system, Academic Press. 139-143.

Kistler A, Mariauzouls C, von Berlepsch K (1998) "Fingertip Temperature as an Indicator for Sympathetic Responses". International Journal of Psychophysiology 29: 35-41.

Stroop J (1935) "Studies of Interference in Serial Verbal Reactions". Journal of Experimental Psychology 18: 643-662.

Toichi M, Kamio Y (2003) "Paradoxical Autonomic Response to Mental Tasks in Autism". Journal of autism and developmental disorders 33: 417-426.

Ming X, Julu P, Brimacombe M, Connor S, Daniels M (2005) "Reduced Cardiac Parasympathetic Activity in Children with Autism". Brain and Development 27: 509-516.

Van Hecke A, Lebow J, Bal E, Lamb D, Harden E, et al. (2009) "Electroencephalogram and Heart Rate Regulation to Familiar and Unfamiliar People in Children with Autism Spectrum Disorders". Child development 80: 1118-1133.

Bal E, Harden E, Lamb D, Van Hecke A, Denver J, et al. (2010) "Emotion Recognition in Children with Autism Spectrum Disorders: Relations to Eye Gaze and Autonomic State". Journal of autism and developmental disorders 40: 358-370.

Yang T, Simmons A, Matthews S, Tapert S, Bischoff-Grethe A, et al. (2007) "Increased Amygdale Activation is Related to Heart Rate During Emotion Processing in Adolescent Subjects". Neuroscience letters 428: 109-114.

Thayer J, Sternberg E (2006) "Beyond Heart Rate Variability". Annals of the New York Academy of Sciences 1088: 361-372.

Mosconi M, Cody-Hazlett H, Poe M, Gerig G, Gimpel-Smith R, et al. (2009) "Longitudinal Study of Amygdala Volume and Joint Attention in 2-to 4-year-old Children with Autism". Archives of general psychiatry 66: 509.

Juranek J, Filipek P, Berenji G, Modahl C, Osann K, et al. (2006) "Association Between Amygdale Volume and Anxiety Level: Magnetic Resonance Imaging (MRI) Study in Autistic Children". Journal of child neurology 21: 1051-1058.

Kleinhans N, Richards T, Weaver K, Johnson L, Greenson J, et al. (2010) "Association Between Amygdala Response to Emotional Faces and Social Anxiety in Autism Spectrum Disorders". Neuropsychologia 48: 3665-3670.

Porges S (2003) "The Polyvagal Theory: Phylogenetic Contributions to Social Behavior". Physiology & Behavior 79: 503-513.

Haznedar M, Buchsbaum M, Wei T, Hof P, Cartwright C, et al. (2000) "Limbic Circuitry in Patients with Autism Spectrum Disorders Studied with Positron Emission Tomography and Magnetic Resonance Imaging". American Journal of Psychiatry 157: 1994-2001.

Coull, J., Frith, C., Frackowiak, R.S.J., Grasby, P.: "A Fronto-Parietal Network for Rapid Visual Information Processing: a PET Study of Sustained Attention and Working Memory". Neuropsychologia 34(11), 1085-1095 (1996).

McAuley, T., Crosbie, J., Charach, A., Schachar, R.: "The Persistence of Cognitive Deficits in Remitted and Unremitted ADHD: A Case for the State-Independence of Response Inhibition". Journal of Child Psychology and Psychiatry (2013).

Verbruggen, F., Logan, G.D.: "Models of Response Inhibition in the Stop-Signal and Stop-Change Paradigms". Neuroscience & Biobehavioral Reviews 33(5), 647-661 (2009).

Baron-Cohen, S., Wheelwright, S., Hill, J., Raste, Y., Plumb, I.: "The Reading the Mind in the Eyes Test Revised Version: A Study with Normal Adults, and Adults with Asperger Syndrome or High-Functioning Autism". Journal of Child Psychology and Psychiatry 42(2), 241-251 (2001).

Jansen, L.M.C., Gispen-de Wied, C.C., Wiegant, V.M., Westenberg, H.G.M., Lahuis, B.E., van Engeland, H.: "Autonomic and Neuroendocrine Responses to a Psychosocial Stressor in Adults with Autistic Spectrum Disorder". Journal of autism and developmental disorders 36(7), 891-899 (2006).

Smeekens, I., Didden, R., Verhoeven, E.: "Exploring the Relationship of Autonomic and Endocrine Activity with Social Functioning in Adults with Autism Spectrum Disorders". Journal of autism and developmental disorders, 1-11 (2013).

Russell, E., Sofronoff, K, Russell, E., Sofronoff, K.: "Anxiety and Social Worries in Children with Asperger Syndrome". Australian and New Zealand Journal of Psychiatry 39(7), 633-638 (2005).

Kerns, C.M., Kendall, P.C.: "The Presentation and Classification of Anxiety in Autism Spectrum Disorder". Clinical Psychology: Science and Practice 19(4), 323-347 (2012).

Porges, S.W.: "The Polyvagal Theory: Neurophysiological Foundations of Emotions, Attachment, Communication, and Self-regulation". WW Norton & Company, New York; London (2011).

Baron-Cohen, S., Ring, H.A., Wheelwright, S., Bullmore, E.T., Brammer, M.J., Simmons, A., Williams, S.C.: "Social Intelligence in the Normal and Autistic Brain: An fMRI Study". European Journal of Neuroscience 11(6), 1891-1898 (1999).

\* cited by examiner

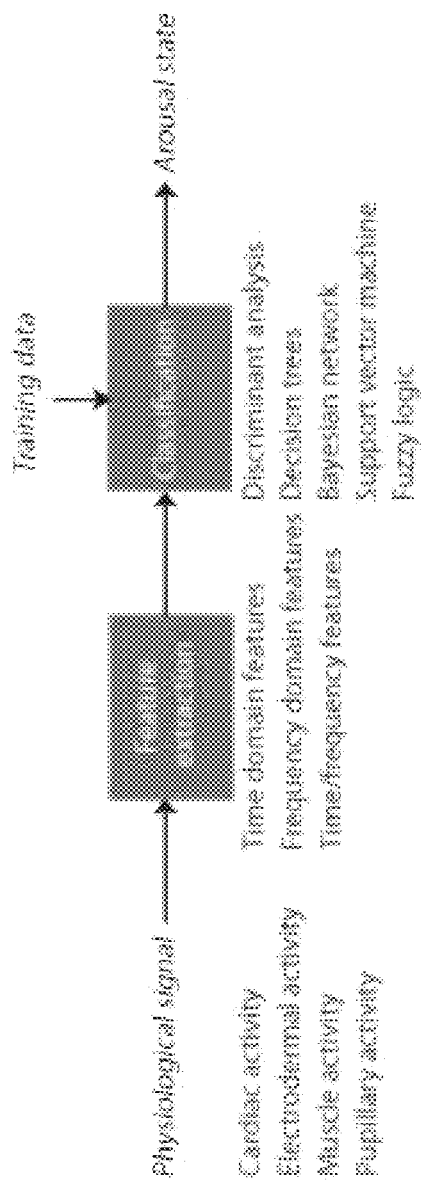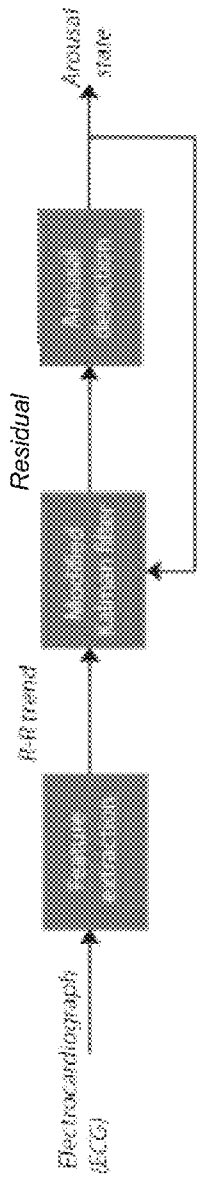

ANXIETY METER

CROSS-REFERENCE TO RELATED APPLICATION

The present disclosure claims priority from U.S. provisional patent application No. 62/021,272, filed Jul. 7, 2014, the entirety of which is hereby incorporated by reference.

FIELD

The present disclosure relates to methods and systems for detection of anxiety using physiological signals from a subject. In particular, the present disclosure may be suitable for detecting anxiety in subjects with autism spectrum disorder (ASD).

BACKGROUND

Anxiety is a state of apprehensive anticipation and is associated with heightened tension, arousal, and negative valence [1]. Automatic detection of anxiety has received attention in several fields including human-computer interaction [2], intelligent transport systems [3], security and access control [4], workload assessment [5], and health monitoring [6]. More recently, automatic detection of anxiety has been suggested as a means to provide an objective measure that can complement clinical anxiety treatment programs [7]. In fact, management of physiological symptoms is an integral part of existing anxiety treatment programs. These programs, however, typically rely on the individual's ability to self-reflect and self-recognize physiological signs of anxiety and are not well-suited to the needs of clinical populations who have intellectual disability and/or deficits in communication, introspection, and emotional self-awareness (e.g., those with autism spectrum disorder (ASD)). In these populations, automatic anxiety detection can serve to reduce some of these barriers to potency and applicability of anxiety treatments by providing individuals with an objective measure of their internal state. However, automatic anxiety detection methods have not been examined in the context of therapeutic settings and clinical populations to date.

Conceptually, anxiety presents across three interconnected dimensions: behavioral (e.g., crying, avoidance, tantrums), subjective-cognitive (e.g., maladaptive and negative thoughts), and physiological [8]. The latter can be non-invasively measured using inexpensive and wearable sensors and has therefore received attention in studies examining automatic detection of anxiety. The physiological response to anxiogenic stimuli has been documented in neurotypical individuals: the stimulus is perceived and interpreted as a threat by structures in the central nervous system, and peripheral and endocrine systems are aroused to mobilize the body's resources for responding to the situation. This arousal response is often accompanied by a series of physiological changes that can be measured non-invasively. These changes include increased cardiovascular activity (e.g., increased heart rate), as well as changes in perspiration (e.g., measured through electrodermal activity) and skin temperature [9]. A technical challenge in detection of physiological arousal is the inter- and intra-personal variations in physiological measures. For example, across individuals, anatomical and neurochemical differences result in variability in basal heart rate and in cardiac reactivity to anxiogenic stimuli. In the same individual, physiological processes (e.g., sinus rhythm and respiratory sinus arrhythmia) and external factors such as diet, sleep, or mental and emotional states also lead to additional heart rate variability.

To model this variability, several studies have used supervised methods that rely on training data and have shown that arousal associated with anxiety can be detected physiologically with high accuracy. For example, time and frequency domain features from 5-minute segments of electrocardiography (ECG), electromyography, respiration, and skin conductivity measurements were used in [3] to classify three stress levels (low, medium, and high) using discriminant analysis. Secondary analysis also showed that heart rate and skin conductance measurements provided the highest correlation with stress levels. In the context of continuous stress monitoring, one-minute segments of ECG, skin conductance, and accelerometer signals were used in [6] to differentiate periods of physical activity from mental stress using three classification schemes (decision trees, Bayesian network, and support network machines). A fuzzy logic system was proposed by de Santos Sierra et al. [4] to classify stress and baseline conditions using skin conductance and heart rate measurements. Zhai and Barreto [2] proposed a support vector machine classifier for detecting stress based on cardiac activity, skin conductance, skin temperature, and pupil diameter.

However, it would be useful to provide a system for detecting anxiety that is not reliant on training data.

SUMMARY

In some example aspects, the present disclosure provides a system for detection of anxiety in a subject, the system comprising: a processor configured to: receive at least one physiological signal that is relevant to a measurement of anxiety; extract at least one feature from the at least one physiological signal, wherein the at least one extracted feature has a value that is affected by the subject's anxiety level; process the at least one extracted feature using a modified Kalman filter, the modified Kalman filter being modified to update a state model using a first weighting of the at least one extracted feature when the at least one extracted feature has a value within a predicted noise model, and to update the state model using a second weighting of the at least one extracted feature when the at least one extracted feature has a value outside of the predicted noise model, the second weighting being less than the first weighting; and provide one or more output signals indicating presence of anxiety when the at least one extracted feature has a value outside of the predicted noise model.

In some example aspects, the present disclosure provides a method for detecting anxiety in a subject, the method comprising: receiving from one or more sensors at least one physiological signal from the subject that is relevant to a measurement of anxiety; extracting at least one feature from the at least one physiological signal, wherein the extracted feature has a value that is affected by the subject's anxiety level; processing the at least one extracted feature using a modified Kalman filter, the modified Kalman filter being modified to update a state model using a first weighting of the at least one extracted feature when the at least one extracted feature has a value within a predicted noise model, and to update the state model using a second weighting of the at least one extracted feature when the at least one extracted feature has a value outside of the predicted noise model, the second weighting being less than the first weighting; and providing one or more output signals indicating presence of anxiety when the at least one extracted feature has a value outside of the predicted noise model.

BRIEF DESCRIPTION OF THE DRAWINGS

Reference will now be made, by way of example, to the accompanying drawings which show example embodiments of the present application, and in which:

FIG. 1 is a block diagram illustrating an example prior art arousal detection system;

FIG. 2 is a block diagram illustrating an example of the present disclosure;

Similar reference numerals may have been used in different figures to denote similar components.

DETAILED DESCRIPTION

Clinical Background

Figure 3:
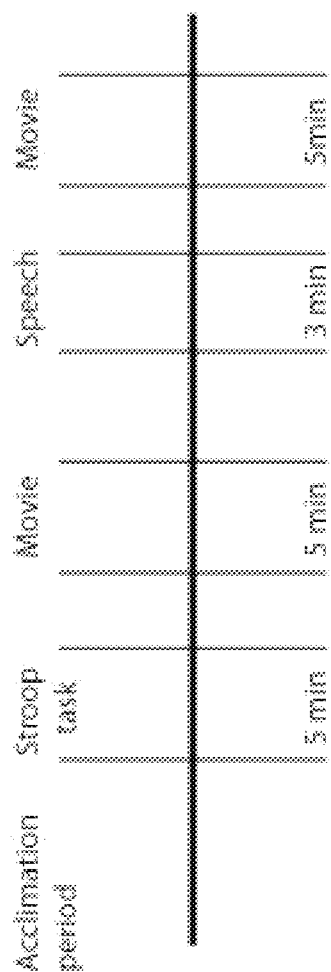
FIG. 3 shows an example protocol used in a study of an example of the present disclosure.

To help in appreciating the present disclosure, a brief discussion of the challenges in detecting anxiety in subjects with ASD is provided below. Although the present disclosure discusses implementation of the disclosed methods and systems for detection of anxiety in a subject with ASD, it should be understood that use of the present disclosure is not limited to this population.

Anxiety symptoms are closely linked to the core deficits of ASD. On the one hand, core-deficits of ASD may contribute to increasing anxiety [37]. Many children with ASD are acutely aware of their social deficits [17], and experience significant anxiety related to inappropriate social behavior and expectations of social failure. Sensory deficits in understanding the external world or awareness of these difficulties [38] may also contribute to increasing anxiety. On the other hand, anxiety may drive and/or exacerbate core deficits in ASD. For example, social anxiety may lead to further avoidance of social situations, promoting isolation from social groups [17]. In fact, anxiety has been correlated with greater degrees of loneliness and social disability [39], decreased participation in school and community [19], and negative externalizing behaviors such as aggression and self-injury [17,40,41]. Moreover, repetitive behaviors seen in ASD, such as hand flapping, rocking, and echolalia, may be anxiety coping mechanisms [38].

Because of the close relationship between ASD and anxiety, assessment of anxiety symptoms in children with ASD is a challenging task. Such assessment typically relies on self-reports or observation of overt behavior. Self-reports are often not reliable in ASD because of deficits in communication as well as difficulties with emotional awareness and introspection [42]. Behavioral symptoms of anxiety are also typically difficult to recognize in ASD due to the symptom overlap between the two conditions as well as the idiosyncratic or atypical nature of anxiety symptoms in this population [42]. These difficulties point to the usefulness of a physiological marker that can reliably document anxiety in ASD.

The physiological response to anxiety is orchestrated by a large network of neural structures in the central, peripheral, and endocrine systems. The peripheral nervous system holds special promise for the development of an anxiety marker as the response of this system can be measured non-invasively and with relative ease. In particular, the autonomic branch of the peripheral nervous system is activated during the anxiety response to mobilize appropriate behavioral responses to stressful stimuli [43]. The autonomic nervous system (ANS) response to stress, known as the fight or flight response, generally involves the activation and inhibition of the sympathetic and parasympathetic branches of the ANS, respectively. This stress response results in several physiological changes that can be measured non-invasively. These include, for example:

Changes in cardiac activity: The sympathetic and parasympathetic branches of the ANS have excitatory and inhibitory effects on cardiac function, respectively. Specifically, activation of the sympathetic system during stress generally increases heart rate and cardiac contractibility [44].

Changes in perspiration: Eccrine sweat glands have predominantly sympathetic cholinergic innervations [45] and their activity increases when the sympathetic nervous system responds to stress. In contrast to thermoregulatory sweating which occurs over the entire body, this type of "emotional sweating" generally occurs in the palms of the hands, as well as the axillae and soles of the feet [46], Because the amount of perspiration affects the electrical conductivity of the skin, sympathetically-induced changes in perspiration can be measured non-invasively as electrodermal activity (EDA). A high correlation between the level of sympathetic activity and phasic changes in EDA has been reported [45].

Changes in skin temperature: Arousal of the sympathetic nervous system generally results in vasoconstriction, roughly proportional to the level of neural activity [47], Furthermore, cutaneous micro-circulation also affects skin temperature, Because arterioles of the fingertip skin have sympathetic, adrenergic constrictor nerves, sympathetically-induced vasoconstriction can be measured indirectly by observing transient changes in fingertip temperature [48].

Example studies, discussed below, were carried out to investigate the ability to detect anxiety in subjects with ASD, using physiological signals.

Example Study 1

A sample of typically developing children (n=18) and children with ASD (n=15) was recruited for the study. Each participant completed an anxiety-inducing task, preceded and followed by a baseline task. For the baseline tasks, participants watched a movie of their choice for 30 minutes. For the anxiety-inducing task, participants completed a computerized version of the Color Stroop (Color-Word Interference) Task [29], commonly used to elicit stress reactions in studies of autonomic nervous system function.

To further characterize the study sample in terms of trait anxiety, the generalized anxiety symptom severity scores from the Child and Adolescent Symptom Inventories were used (child version was used for children 12 or younger and the adolescent version was used otherwise). Participants also completed the State-Trait Anxiety Inventory (STAI) as a self-reported measure of state anxiety. The STAI was completed before and after each baseline.

Physiological signals measured in this example study included blood volume pulse (BVP), electrodermal activity (EDA), and skin temperature signals. Sensors were attached to the non-dominant hand using breathable tape (for BVP and skin temperature) and velcro straps (for EDA). To measure BVP, a photoplethysmography sensor was attached to the palmar surface of the distal phalanges of the first digit of the hand. EDA was measured as skin conductance using a pair of 10 mm diameter dry Ag—AgCl electrodes secured to the palmar surface of the proximal phalanges of the second and third digits of the non-dominant hand. Skin temperature was measured using a thermistor fastened to the palmar surface of the distal phalanx of the fourth digit of the hand.

The self-report (STAI) and physiological measures confirmed that the Stroop task successfully elicited a stress-response in both the ASD and TD groups. The STAI results further indicated that the levels of perceived anxiety did not differ significantly between the groups. This result is encouraging as differences in the perceived level of stress have been suggested to affect findings of previous studies of physiological function in children with ASD. Caution must be taken in interpreting this finding given the known deficits in introspection, emotion awareness, and communication of emotions in ASD [42].

The anxiety condition (Stroop task) was found to cause significant increases in heart rate and tonic levels of EDA in both groups, a pattern consistent with the expected ANS arousal in response to stress. This further confirms that the anxiety condition did in fact elicit an anxiety response in both groups.

Results from this example study suggest that state anxiety may be detected based on measurement of ANS signals, further supporting the feasibility of using these physiological signals as language-free and objective indicators of anxiety in children with ASD. This is important as recognition of anxiety symptoms in ASD, especially in lower-functioning individuals, is a challenging task. The challenge relates to the symptom overlap between ASD and anxiety disorders (e.g., panic attacks and obsessions), idiosyncratic or atypical anxiety symptoms, and limited understanding of subjective experiences of anxiety due to deficits with communication and introspection [42]. The difficulties in recognition of anxiety symptoms can lead to diagnostic overshadowing [42] and complicate treatment of anxiety in ASD. A physiological measure of anxiety can partially overcome these difficulties and complement existing assessment methods.

The ASD group was found to have elevated heart rate compared to the TD group for the movie watching and Stroop tasks. The cardiac response is determined by the inhibitory and excitatory effects of the parasympathetic and sympathetic branches of the ANS, respectively. Therefore, the finding of elevated heart rate may indicate the under-arousal of the parasympathetic system and/or over-arousal of sympathetic nervous system. Reduced parasympathetic tone and increased sympathetic tone during rest [51], a blunted parasympathetic response during a mental task (mental arithmetic) [50], and lowered levels of respiratory sinus arrhythmia (measure of parasympathetic activity) [52, 53] have been previously reported in ASD. This evidence collectively suggests decreased parasympathetic activity in ASD, which can lead to an over-aroused cardiac ANS response.

The EDA response patterns provide further insight into the activity of the sympathetic nervous system as the palmar eccrine sweat glands are largely sympathetically innervated. In this study, it was found that the number of EDRs during the first movie watching period was higher than typical for the ASD group. Moreover, unlike the TD group, the number of EDRs did not increase during the Stroop task for the ASD group. This pattern is consistent with the hyper-arousal of the sympathetic nervous system resulting in decreased responsivity to stress.

The results did not indicate any significant differences between the ASD and TD groups in the mean EDA level (reflects tonic sympathetic activity). It may be that tonic EDA is an indicator of general states of arousal whereas phasic EDRs are useful for studying differences related to behavioral and psychopathological states [45]. As such, the mean EDA measure may not be sensitive to differences between the two groups studied herein.

There is evidence to suggest that the production of the EDRs due to affective processes is centrally mediated by the limbic structures, including the anterior cingulate cortex (ACC) and the amygdala [45,46]. ASD is associated with structural and functional differences in the amygdala. Atypical findings in the ACC have also been reported in the ASD. These include decreased volume and diminished activation in the ACC [60]. These regions may therefore be interesting targets for future investigations of ANS function in ASD.

Sympathetic stimuli are typically expected to induce vasoconstriction in arterioles of the fingertip skin, leading to a decrease in skin temperature [48]. In this study, the results did not indicate significant differences in skin temperature between the ASD and TD groups during the movie-watching periods. However, unlike the TD group who exhibited a decrease in skin temperature during anxiety, skin temperature did not change significantly in the ASD group. This finding may be explained by chronic over-arousal of the sympathetic nervous system (vasoconstriction), resulting in decreased responsivity of the ANS.

Although there are no direct studies of vasoconstriction mechanisms in ASD, increased vasoconstriction due to hyper-arousal of the sympathetic system has been suggested previously as an explanation for elevated resting heart rate, diastolic blood pressure, and mean arterial pressure observed in ASD [51]. Another explanation for the results may be the potential pathology of the adrenergic constrictor nerves that hamper vasoconstrictor mechanisms in ASD.

The results of this study generally support the feasibility of using a physiological marker to detect anxiety in children with ASD based on patterns of ANS function.

Example Study 2

In this study, a sample of typically developing (TD) children (n=36) and children with ASD (n=47) was recruited. After consent, participants completed a 2-hour study in one session. During the session, they sat in front of a computer screen and completed five tasks, each preceded and followed by a baseline task. The tasks were:

Color Stroop (Color-Word Interference) test [49]: This task was used to elicit an ANS stress reaction, and shown to elicit both psychological and physiological arousal responses in typically developing populations as well as children with ASD. Participants completed a computerized, single-trial version of the task which involved the presentation of words corresponding to color names, printed in differently colored letters. The participants were required to name the color of the letters while ignoring the printed word. The task consisted of 5, one-minute blocks in which stimulus presentation frequency varied from 2 to 1.25 seconds/word (blocks one and five: 2 seconds/word, blocks 2 and 4: 1.5 seconds/word, block 5: 1.25 seconds/word). During the first and last blocks, only congruent stimuli were presented, whereas the remaining blocks consisted of only incongruent stimuli. Prior to starting the task, participants were provided with 10 practice stimuli to ensure understanding of the task. Performance on this task was measured as the percentage of correct responses.

Public speaking: For this task, participants were given 2 minutes to prepare a 3-minute talk on a topic of their choice. The talk was then delivered to 3 strangers. Public speaking tasks have been successfully used in previous studies examining cardiac responses to anxiogenic stimuli in neurotypical individuals and in children with ASD. Performance on this task was measured as the percentage of the time the participant did not speak or vocalize during the task.

Rapid visual information processing (CANTAB, http://www.camcog.com/): In this test of sustained attention and working memory [61], participants were presented with random single-digit numbers (2-9) at rate of 100 digits per minute and asked to identify a pre-specified 3-digit sequences (e.g., 3-5-7) by pressing the space bar. The duration of this task was four minutes. Performance was measured as the percentage of correctly identified sequences.

Stop signal task [62]: This was a test of response inhibition. Participants were presented with a series of Xs and Os and asked to press the left and right buttons on a gamepad when Xs and Os appeared, respectively. The stimuli were occasionally followed by an auditory tone (stop signal), requiring the participants to withhold their response. The task consisted of 5 blocks, with 24 trials per block. The first block was practice. Total length of task was approximately 10 minutes. Task performance was measured as the latency of the stop process (stop task reaction time (SSRT)) in milliseconds [63].

Reading the Mind in the Eyes—child version [64]: This was a test of social cognition (theory of mind) where participants were presented with a set of 28 photographs depicting the eye region of the face, and asked to choose the word that best described what the person was thinking or feeling from a set of four choices. Performance was measured as the number of correct responses.

For the baseline task, participants watched clips of animated movies. All baseline tasks were 5 minutes in duration, except for the initial baseline which was 15 minutes long to allow acclimation to the environment and sensors.

Figure 9:
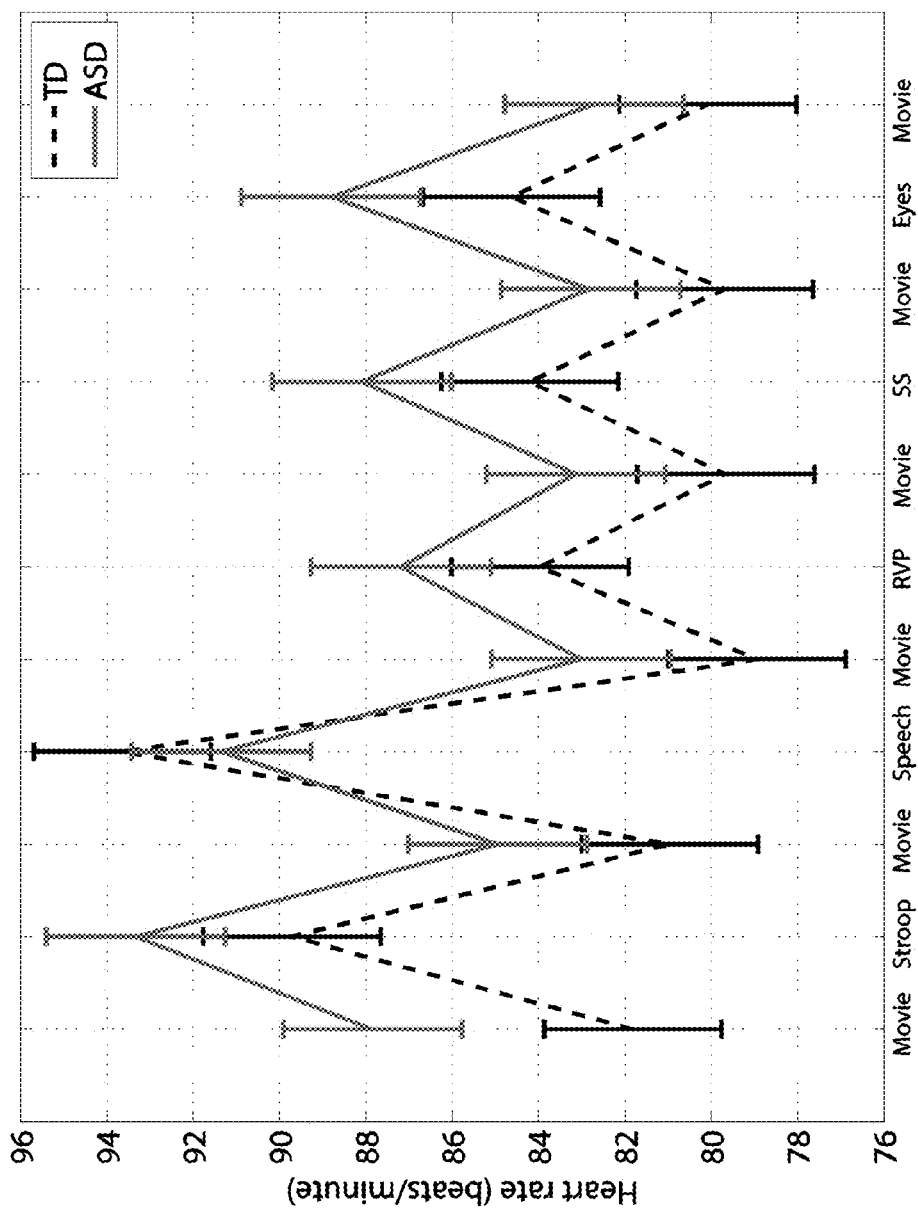
FIGS. 9 and 10 are charts illustrating example differences in physiological signals between typically developing subjects and subjects with ASD.
Figure 10:
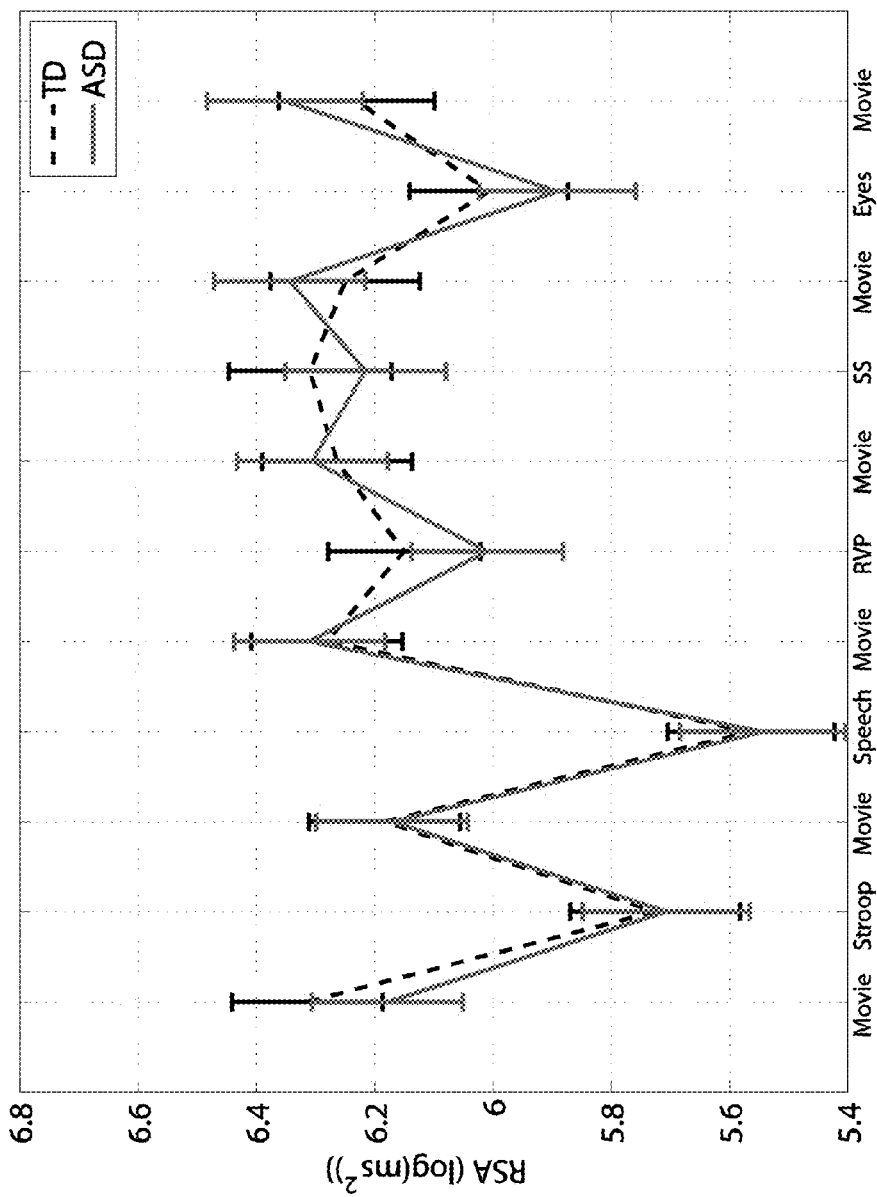

FIG. 9 shows example measurements of heart rate in the TD and ASD groups, during the session. FIG. 10 shows example measurements of respiratory sinus arrhythmia (RSA) in the TD and ASD groups, during the session. As discussed below, these results illustrate detectable significant differences in physiological signals when a subject experiences anxiety.

The results suggest atypical cardiac findings in the ASD group despite group differences on task performance. These findings include cardiac hyperarousal in the ASD group as well as atypical responses to the public speaking and Reading the Eyes in the Mind tasks. In particular, while not statistically significant, the ASD group was found to have an elevated heart rate during the experimental session. Moreover, this group showed a blunted heart rate response to public speaking which was correlated with full-scale IQ and generalized anxiety score, and an exaggerated RSA response to the Reading the Eyes in the Mind task which was correlated with full-scale IQ.

The data showed a blunted HR response to the social anxiety task in the ASD group. This pattern has been reported consistently in three studies examining ANS reactivity to psychosocial challenges [33, 65, 66], and previously suggested to be a manifestation of response saturation due to basal hyperarousal. Consistent with this hypothesis, a significant negative association was found between HR change and scores on the generalized anxiety subscale of the RCADS. This atypical response, however, has not been previously reported in ANS studies of public speaking involving social phobics, and may therefore be unique to ASD. The blunted response was not seen in the second anxiety task (Stroop Color-Interference task). Given that impairments in social interaction are a defining feature of ASD, it may be that the atypical response found in this study may reflect differences in subjective experiences of the task (e.g., motivation, attention, or judgment of the social threat). This would be consistent with the finding of a positive correlation between HR change, and IQ and task performance [67, 68].

The data also revealed increased RSA reactivity to the Reading the Mind in the Eyes task in the ASD group. This task is a test of theory of mind (ToM) or the ability to recognize others' emotions and states of mind. A domain affected in ASD, ToM allows for fostering of appropriate social behaviors, establishment of reciprocal relationships, and development of social competence [53]. Social function, and ToM in particular, have also been linked to RSA regulation as the "vagal brake" promotes calm behavioral states that are needed for social function, with greater ability to reduce RSA associated with better outcomes [69]. While an association was not found between severity of social communication symptomatology as measured by the SCQ, the data did show that IQ was a significant predictor of RSA change in the ASD group. In the absence of performance differences between the groups, large RSA variability may reflect higher degree of effort or compensatory mechanisms applied by the ASD group. The latter is consistent with atypical central nervous system responses to the Eyes task (e.g., decreased amygdala activation) [70].

It has been suggested that ASD may be associated with autonomic dysregulation. The data are consistent with this hypothesis. In particular, the example results indicate basal heart rate hyperarousal and atypical heart rate and respiratory sinus arrhythmia reactivity to two social tasks (public speaking and Reading the Mind in the Eyes).

The above example studies illustrate the experimental data supporting the ability to detect anxiety in children with ASD using non-invasive physiological data.

Conventional methods and systems for detecting anxiety typically use supervised learning approaches that rely on training data, which may be impractical to obtain in clinical populations. For example, obtaining training labels in populations with communication and introspection challenges is a very challenging task. Moreover, training data must be regularly updated to reflect time-variations in physiological measures. This is a requirement that may not be suitable for implementation in therapeutic settings where the device is used continuously over long periods of time.

In some examples, the present disclosure provides a real-time unsupervised method for physiological detection of arousal associated with anxiety and a system for implementing the same. By real-time, it is meant that detection of anxiety (and optionally feedback output indicating detection of anxiety) occurs substantially at the moment that the subject is experiencing anxiety, such as at the moment of onset of anxiety. By unsupervised, it is meant that there is no reliance on learning or training data, and possibly no need for involvement of a clinician or nurse in order to detect anxiety.

This disclosure also provides discussion and evaluation of an example algorithm using data from children with ASD. In some examples, the disclosure provides an unsupervised and real-time implementation of a physiological anxiety detection system, and the evaluation of such an example system in a clinical population.

Mathematical Background

The arousal detection problem may be modeled as a problem of choosing a class $\zeta_k \in \{0, 1\}$ (0: arousal, 1: baseline) at time k given a set of physiological measurements. FIG. 1 shows an overview of typical existing arousal detection systems. The input to the system is a physiological signal known to change with anxiety-related arousal as discussed elsewhere in the present disclosure. The signal is then processed to extract time, frequency, and time/frequency features correlated with arousal. These features serve as the input into a classification system which decides if the observed features belong to a baseline or arousal class. The conventional classification system involves learning a representation of the two classes and a decision rule for determining which of the two classes best explains the measurement. Further details of classification algorithms are discussed below.

Physiological Features of Anxiety

The anxiety response involves both the central and peripheral nervous systems. At the central level, cortical and subcortical structures (e.g., amygdala) perceive an anxiogenic stimulus as a threat and mobilize the body's fight or flight response. At the peripheral level, this response manifests as the arousal of the ANS. The ANS is involved in involuntary control of the viscera, and as such its function can be indirectly quantified by measuring visceral functions. Examples of such functions include cardiac activity, electrodermal activity (measuring function of eccrine sweat glands), skin temperature (measuring cutaneous vasoconstriction), and pupillary activity. Among these, cardiac activity has received much attention in studies of the ANS fight or flight response. Autonomic control of the heart is achieved through sympathetic and parasympathetic influences on the cardiac muscle, regulating the length of time between consecutive heartbeats. As such, the cardiac ANS effect is often quantified by the length of the inter-beat intervals, known as the R-R intervals. The fight or flight response arouses the sympathetic branch of the ANS and suppresses the parasympathetic branch. This leads to a decrease in R-R intervals and an increase in the heart rate. Sympathetic influences on the heart occur rather slowly (0.04-0.15 Hz), whereas parasympathetic influences have a shorter response latency (0.15-0.4 Hz) [10].

Arousal Detection

Conventional arousal detection systems typically learn statistical models for baseline and arousal classes [3], [6], [4] or determine decision boundaries in the measurement space that separate these classes [6], [2]. As previously mentioned, these approaches typically require training samples from both classes prior to and during system use.

In some examples, the present disclosure provides an unsupervised algorithm for modeling time-varying and stochastic variations in basal physiological activity and for detecting arousal-related deviations from this baseline model. In contrast to conventional approaches, the present disclosure provides a single model for baseline activity and arousal-related deviations may be detected from this model. In some examples, a Kalman filter is used to adaptively estimate a model for baseline physiological signal of interest given a set of noisy measurements of that signal.

Mathematically, denote the physiological signal at time k as $x_k$ and its noisy measurement as $y_k$. The Kalman filter tracks the first two moments of the density $f(x_k | y_k, \ldots, y_0)$ over time. At every time point, the Kalman filter operates in two phases. In the first phase, a system equation modeling the time dynamics of the state is used to predict the state variable based on previous estimates. During the second phase, observed measurements are used to further refine the state estimate. The second phase relies on a measurement equation which relates the state variable to the measurements. This step also produces a set of residuals (also referred to as "innovations") that quantify how closely the measurement matches the state prediction. These residuals may be used to detect deviations from the baseline model.

Example Method and System

FIG. 2 shows an overview of an example of the disclosed method. The details of each block are discussed in the following sections.

Feature Extraction

The example method of FIG. 2 uses R-R intervals obtained through electrocardiography (ECG) as the physiological measure of arousal. This choice was based on previous work showing significant changes in R-R intervals during anxiety [7], however other physiological signals may be used additionally or alternatively. For example, suitable physiological signals that may be used include other signals indicative of cardiac activity, electrodermal activity (e.g., measuring the function of eccrine sweat glands), skin temperature (e.g., measuring cutaneous vasoconstriction), and pupillary activity, among others.

In some examples, feature extraction may include removal of artifacts, such as noise, baseline wandering, motion artifacts and electrical noise, among others. A filter, such as a bandpass filter, may be applied as appropriate to remove such artifacts. Other techniques may be used.

Although this example method is described as using a single physiological signal, other examples may use multiple physiological signals and/or one or more signal(s) formed from a combination of physiological signals, as input. Use of a combination of physiological signals may result in more accurate detection of anxiety and may help to avoid false positives or false negatives, and may help to increase sensitivity of detection.

In examples where anxiety detection is carried out in real-time, frequency-based ECG features (e.g., respiratory sinus arrhythmia) may not be used, although such frequency-based signals may be used in other examples where detection may be near real-time or with slight time delay. Use of a frequency-based signal may require the signal to be analyzed over a time period, for example by using a moving window to process such a signal.

As previously mentioned, sympathetic and parasympathetic changes in R-R intervals are relatively slow-varying. As such, a slowly-varying R-R trend may be calculated as the average of R-R intervals in overlapping windows in time:

$$y_k = \frac{1}{W} \sum_{t=k-W}^{k} RR_t \qquad (1)$$

In the above equation, $$\{RR_t\}_{t=0}^{T}$$

are the R-R intervals extracted from the ECG signal, and W is the window length of the running average used for computing the R-R trend. Given that $y_k$ are computed from overlapping time windows, we have k≤T.

Detection Algorithm

The conventional basic Kalman filter assumes that the state $x_k$ can be described by a single, linear Gaussian model. This assumption is violated in the disclosed example method where changes occur in heart-rate dynamics due to switching between baseline and arousal states (e.g., increased R-R mean and variance as well as changes in persistent heart rate rhythms). The practical implication of this violation is that, according to conventional implementations of the Kalman filter, R-R values measured during arousal states would continue to update the baseline state, causing an undesirable drift in the baseline model and potentially divergence of the filter.

Several extensions of the Kalman filter have been proposed to deal with switching models (e.g., multiple model estimators [11], Markov jump linear models [12]). However, these approaches require the a priori specification of system dynamics for both the baseline and arousal classes. While system dynamics are generally known for baseline heart rate activity [13], arousal dynamics are subject to significant inter- and intra-personal variations and cannot be easily modeled.

In the present disclosure, a modified Kalman filtering algorithm is used instead of the conventional basic Kalman filter and the above-noted extensions of the Kalman filter. In this approach, a single Kalman filter is used to track and update baseline activity, but R-R measurements during arousal states are considered to be "unreliable" measurements which are not used for state refinement. This approach may enable modeling of multiple system dynamics without the need for the explicit specification of multiple models.

The Modified Kalman Filter

The traditional Kalman filter assumes that the data follows a fixed model (e.g., constant heart rate). This poses a challenge in applications where data follow multiple models. Consider, for example, the disclosed example for detection of anxiety using heart rate. The heart rate time series follows a "constant" model during baseline, but undergoes a mean change during arousal states. In order to address this challenge, a modified version of the Kalman filter may be used that allows for incorporation of multiple models (e.g., baseline and arousal). This modified filter essentially changes the "uncertainty" associated with the measurement to achieve this purpose. In particular, the uncertainty associated with measurement is increased during an arousal state. This allows the filter to eliminate the influence of the measurements on system estimates when a model change occurs, essentially making the filter robust to computational difficulties that arise with the traditional Kalman filter during model changes.

The state-space model that governs the prediction and update steps of the Kalman filter is first described. The example disclosed method makes use of a state model that models the behavior of a system, assuming a constant R-R trend perturbed by zero-mean, white, Gaussian noise [13], [14], [15]. This type of random walk model may be suitable for slowly drifting signals where a statistical model based on domain knowledge is unavailable [15]. In the example method, the linear-Gaussian model may capture small variations related to the normal sinus rhythm [13]. The measurement model may relate the observed R-R measurement to the state hypothesized by the state model. A linear model may be assumed, which accounts for measurement uncertainties through the inclusion of additive, white, Gaussian noise. Mathematically, the system and measurement equations are:

$$x_k = x_{k-1} + w_k, \qquad (2)$$

$$y_k = x_k + v_k, \qquad (3)$$

where, the state variable $x_k$ is the ideal slowly-varying R-R trend at time k, and y(k) is defined in Equation (1). The system and measurement noise processes $w_k$ and $v_k$ are traditionally defined as zero-mean, white, Gaussian noise with known covariances $Q_k$ and $R_k$ $$f(w_k) = N(0, Q_k), \qquad (4)$$

$$f(v_k) = N(0, R_k). \qquad (5)$$

To deal with the switching model challenge, the problem may be formulated as estimating the state of a system in which the arrival of arousal states is modeled as a Bernoulli process. Therefore, at time k, the arrival of the arousal state, $\zeta_k$ is a binary random variable with parameter $0 < \lambda < 1$ (i.e., $p_{\zeta_k}(1) = \lambda$). Independence of binary variables $\zeta_k$ and $\zeta_j$ for k≠j is assumed.

The measurement covariance $R_k$ may then be manipulated based on the state $\zeta_k$. In particular, when the example system is in an arousal state (i.e., $\zeta_k = 0$), $R_k$ is increased. This increase in uncertainty of measurements allows the system to reduce the influence of measurements on the final estimate during the refinement step of the Kalman filter. Mathematically, the measurement noise may be defined as:

$$f(R_k | \zeta_{k-1}) = \begin{cases} (0, \Sigma_k), & \zeta_{k-1} = 1 \\ (0, N\Sigma_k), & \zeta_{k-1} = 0 \end{cases} \qquad (6)$$

where N≥1 is an integer multiplier of the noise covariance. The analysis in [16] can be used to arrive at the formulation of a modified Kalman filter for the example model described above. Denote the state estimate and its covariance at time j given observations $y_0 \ldots y_i$ as $\hat{x}_{j|i}$ and $P_{j|i}$, respectively. Then, given the above formulation, the state estimate and its covariance are computed by the modified Kalman filter as follows [16]:

Prediction $$\hat{x}_{k+1|k} = \hat{x}_{k|k}$$

$$P_{k+1|k} = P_{k|k} + Q_k$$

Update $$\epsilon_k = y_k - \bar{x}_{k+1|k}$$

$$G_k = P_{k+1|k}(P_{k+1|k} + \zeta_k R + (1-\zeta_k)N\Sigma_k)^{-1}$$

$$\hat{x}_{k+1|k+1} = \hat{x}_{k+1|k} + G_k \epsilon_k \quad (7)$$

$$P_{k-1|k+1} = P_{k+1|k} - G_k P_{k+1|k} \quad (8)$$

The initial values $\hat{x}(0|0)$ and $P(0|0)$, and the noise covariances $Q_k$ and $\Sigma_k$ are determined from the data.

Estimation of Arousal Level

As a by-product of the estimation procedure, the Kalman filter provides an error term $\epsilon_k$, also referred to as the innovation or the residual, that quantifies deviations from the assumed baseline model. Note that a decrease in the R-R trend is expected during arousal conditions. The magnitude of the decrease in residuals is used to determine if deviations from the model are significant enough to be considered arousal. To achieve this, the following detection algorithm is used:

$$\zeta_k = \begin{cases} 1, & \text{if } \frac{\bar{\epsilon}_k - \mu_k^\epsilon}{\sigma_k^\epsilon} \geq \tau \\ 0, & \text{if } \frac{\bar{\epsilon}_k - \mu_k^\epsilon}{\sigma_k^\epsilon} < \tau \end{cases}, \quad (9)$$

where $\tau$ is a detection threshold and:

$$\bar{\epsilon}_k = \frac{1}{W_\epsilon} \sum_{i=k-W_\epsilon}^{k} \epsilon_i \quad (10)$$

$$\mu_k^\epsilon = \frac{1}{k+1} \sum_{i=0}^{k} \epsilon_i \quad (11)$$

$$\sigma_k^\epsilon = \frac{1}{k} \sum_{i=0}^{k} (\epsilon_i - \mu_k^\epsilon)^2 \quad (12)$$

The above algorithm estimates the short residual mean as well as the long-term distribution of the residual terms. The short-term mean $\bar{\epsilon}_k$ is then compared against the expected distribution for the baseline class.

In conventional classical Kalman filtering, the residual sequence is zero-mean and white with a known covariance. Assuming residuals follow a Gaussian distribution with first and second moments specified above, standard statistical tables can be used to determine the threshold $\tau$ such that:

$$\text{Prob}(\bar{\epsilon}_k < \tau) < 1 - \alpha \quad (13)$$

where $\alpha$ is a pre-specified level for statistical significance. Given the modeling uncertainties in estimating $Q_k$ and $R_k$ as well as model violations during arousal states, however, it may be expected that the residuals computed by the modified Kalman filter of the example system will not follow a standard parametric distribution. Accordingly, $\tau$ may instead be determined experimentally.

Comments on the Modified Kalman Filter

1) Stability:

In the context of systems with intermittent observations, Sinopoli et al. [16] derived stability conditions for the above filter for linear-Gaussian systems. Adopting that analysis for the proposed system when $N \to \infty$, it is noted that if the probability of arrival of a baseline state is $\lambda > 0$, then the expectation of the estimation error covariance is finite.

2) Special Cases:

For N=1, the above-discussed modified Kalman filter is equivalent to the traditional Kalman filter as the gain $G_k$ reduces to:

$$G_k = P_{k+1|k}(P_{k+1|k} + R)^{-1} \quad (14)$$

For $N \to \infty$, $G_k \to 0$ when $\zeta_k = 0$. Therefore, the modified Kalman filter operates as a traditional Kalman filter in baseline states (i.e., $\zeta_k = 1$). However, in an arousal state, the modified Kalman filter does not perform any measurement updates, unlike the traditional Kalman filter. That is, the system prediction is simply propagated forward.

3) Sub-Optimality:

The above formulation relies on several assumptions that may be violated when used for detection of anxiety. These include the independence of system and measurement noise, as well as that of the binary variables $\zeta_k$. Nevertheless, experimental results (discussed below) indicate that the disclosed example method provides reasonable accuracy in estimating arousal states.

In this way, the anxiety state of a subject may be modeled as a system having a baseline state (i.e., anxiety is not present or is negligible) and an arousal state (i.e., anxiety is present and non-negligible). The input to this system includes at least one physiological signal relevant to measurement of anxiety in a subject. In the implementation of the modified Kalman filter described above, the state model may be updated using the subject's physiological signal when the residual value does not deviate significantly from the baseline model (e.g., when the physiological signal falls within the predicted noise model). Where the residual value deviates significantly from the baseline model (e.g., when the physiological signal falls outside of the predicted noise model for the baseline), the physiological signal is not used to update the state model. Instead, this is determined to be indicative of the arousal state, which is associated with physiological signals outside the expected range of baseline values. Output signals can then be generated accordingly, indicating the presence of anxiety. Such output signals may be transmitted to another system and/or used to provide feedback to the subject and/or a clinician, for example.

Example System

Figure 11:
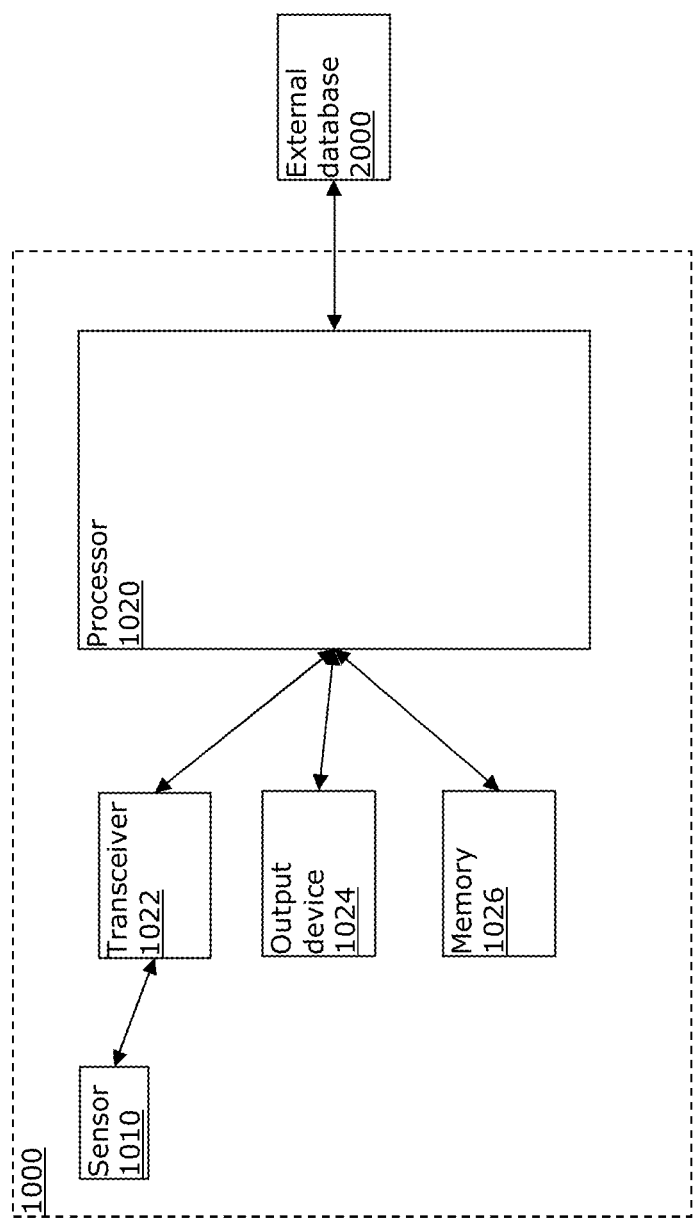
FIG. 11 is a schematic diagram showing a system for detecting anxiety, in accordance with an example of the present disclosure.

In some examples, the present disclosure provides an example system or device for carrying out the method described above. FIG. 11 shows an example of such a system.

The example system 1000 may include one or more sensors 1010 that may be positioned on or near the subject for detecting physiological signals relevant to measurement of anxiety. Any suitable sensor(s) may be used, such as wearable heart rate sensors or electrodes. Signals from the sensor(s) 1010 may be transmitted (e.g., wired or wirelessly) to a processor 1020 that processes the signals using the modified Kalman filter approach described above and determines whether anxiety is present in the subject. The processor 1020 may be in communication with a transceiver 1022 for receiving signals from the sensor(s) 1010. The transceiver 1022 may also be used by the system 1000 to communicate with external systems (e.g., one or more external databases 2000). The processor 1020 may cause an output device 1024 to provide output, such as feedback as described below. The processor may communicate with one or more internal or external memories 1026. The memory(ies) 1026 may store executable instructions for implementing the method described above, including the modified Kalman filter. The memory(ies) 1026 may also store databases of relaxation techniques, a subject's history of anxiety, a log of occurrences of detected anxiety, and other information about the subject, as well as patterns of physiological activity in the subject or larger populations, for example.

In some examples, the sensor(s) 1010 may be integrated with the processor 1020 in a single device, for example as a wearable biosensor to be worn by the subject (e.g., on the wrist). In such an embodiment, the sensor 1010 may be able to communicate directly with the processor 1020 without going through the transceiver 1022.

The example system 1000 may provide feedback to the subject and/or a clinician about the arousal state of the subject. For example, after the physiological signal from the sensor(s) 1010 has been processed by the processor 1020, the processor 1020 may transmit signals (e.g., wired or wirelessly) to the output device 1024, such as a display and/or a speaker. The output device 1024 may then provide visual and/or audio feedback indicating the subject is experiencing anxiety. In some examples, the output device 1024 may be integrated with the processor 1020 in a single device, such as a portable electronic device, which may be a handheld electronic device (e.g., a smartphone) or a wearable electronic device (e.g., computerized eyeglasses or wrist devices).

Figure 12:
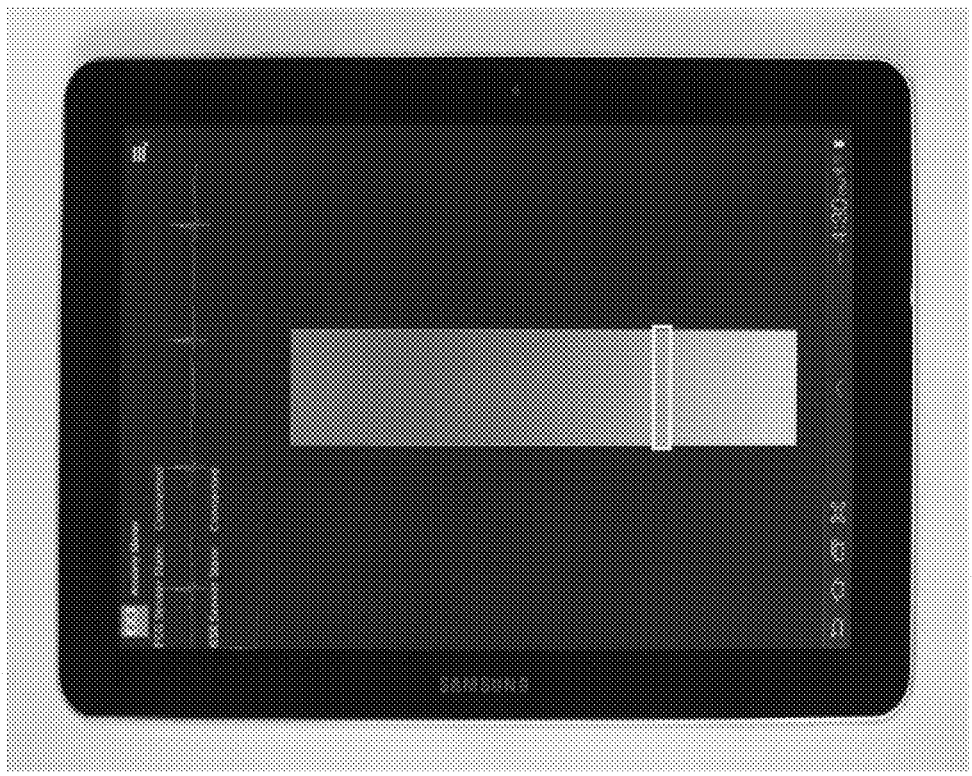
FIG. 12 shows an example of visual feedback provided by a system for detecting anxiety, in accordance with an example of the present disclosure.

FIG. 12 shows an example of such a device, in the form of a smartphone providing visual feedback. In this example, visual feedback may be presented to be viewed by the subject and/or a clinician in the form of a colored bar shown on the display screen. A slider or other indicator on the bar may move towards red (indicating anxiety) or green (indicating no anxiety) depending whether the processor 1020 determines anxiety to be present or not. In this example, the subject's heart beat as detected by a heart rate sensor is also shown. The feedback provided may be substantially language-free or language-neutral, which may enable a young subject, a language-challenged subject or a cognitively-challenged subject to easily understand the feedback provided.

Other techniques for providing feedback may be used. For example, the feedback may include audio feedback, tactile feedback, visual feedback, or a combination of these. Visual feedback may include a color changing circle, a worry bug that wakes up or goes to sleep, or a thermometer-like indicator.

In addition to feedback indicating the presence of anxiety, the example system 1000 may further provide output to the subject and/or the clinician to help the subject return to a state of lessened or no anxiety. Such further output may be in the form of visual or audio suggestions of relaxation techniques (which may be pre-stored in the memory(ies) 1026), for example. The subject's physiological signals may be monitored while this guidance is provided, so that the success of the relaxation technique may be determined. If anxiety continues to be detected despite the relaxation guidance provided, different relaxation techniques may be suggested. Conversely, if the system 1000 detects that the subject is returning to a state of lessened or no anxiety, encouragement may be provided.

In some examples, the system 1000 may create a log of the subject's anxiety state and may store the log in an internal or external memory 1026 and/or transmit the log to the external database 2000 for analysis. Information included in such a log may be useful to help the subject and/or clinician to identify anxiety triggers and successful relaxation techniques, for example.

The present disclosure may be embodied in a portable electronic device, which may be a handheld electronic device such as a mobile phone, a smartphone, a tablet, or may be a wearable electronic device (e.g., computerized eyeglasses, watch or bracelet), for example. Such a device may be carried or worn by the subject during daily activities and may thus be able to provide real-time monitoring of the anxiety level of the subject, as well as being able to provide real-time feedback to the subject and/or clinician about the arousal state of the subject. In some examples, the present disclosure may be implemented in conventional portable electronic devices and using conventional physiological sensors.

In some examples, the system 1000 may include any suitable off-the-shelf physiological sensor 1010 (e.g., a wearable sensor such as the Shimmer™ sensor) and any suitable consumer portable electronic device. A downloadable software application (also referred to as an app) for implementing the disclosed method may be installed onto the electronic device. The software may be updated as appropriate to incorporate new relaxation techniques, different numbers and/or types of physiological sensors, and/or new feedback techniques, for example.

Example Study

The accuracy of the example disclosed system was evaluated in a study using data from a sample of children with ASD (n=24).

The data used herein are a subset of data from a previous study examining autonomic function in children with ASD [22]. This subset was created by excluding children who were on medications that affect autonomic function (n=8) and those who exhibited an atypical ANS response to anxiety (i.e., less than one beat/minute change in heart rate in response to anxiogeous stimuli) (n=5). Data from three additional participants were excluded as one did not complete the public speaking task and for the other two, the R-R noise removal algorithm detected over 5% noise corruption in the ECG record.

Participants

An expert, reliable research team diagnosed each participant using the DSM-IV criteria supported by the Autism Diagnostic Observation Schedule (ADOS) [23] and the Autism Diagnostic Interview-Revised (ADI-R) [24]. Wechsler Scales of Intelligence (Wechsler Abbreviated Scale of Intelligence (I and II), and the Wechsler Intelligence Scale for Children IV) and the Social Communication Questionnaire were used to assess intellectual functioning and ASD symptom severity, respectively. Anxiety symptomatology was characterized with respect to five DSM-IV anxiety disorders (separation anxiety disorder, social phobia, generalized anxiety disorder, obsessive-compulsive disorder, and panic disorder) using the parent version of the Revised Child Anxiety and Depression Scale (RCADS-P) [25]. Participant characteristics are summarized in Table I below:

| Domain | Measure | Mean ± SE |
| --- | --- | --- |
| Demographics | Age | 11.7 ± 2.8 |
|  | Full-scale IQ | 95.6 ± 18.6 |
|  | Sex (male:female) | 17:7 |
| ASD Symptomatology | SCQ | 18.6 ± 7.8 |
| Anxiety | RCAD-SAD | 62.7 ± 18.3 |
| Symptomatology | RCAD-GAD | 56.9 ± 16.5 |
|  | RCAD-PD | 56.7 ± 18.6 |
|  | RCAD-SP | 49.3 ± 9.5 |

-continued

| Domain | Measure | Mean ± SE |
|---|---|---|
| | RCAD-OCD | 53.1 ± 8.3 |
| | RCAD-total anxiety | 56.5 ± 14.9 |

Participant characteristics: SCQ—Social Communication Questionnaire; SAD—Separation Anxiety Disorder; GAD—Generalized Anxiety Disorder; PD—Panic Disorder; SP—Social Phobia; OCD—Obsessive Compulsive Disorder Tasks FIG. 3 provides an overview of the experimental protocol used in this example study. The data were obtained as part of a larger protocol described in detail in [22]. Participants completed two anxiogenic tasks while seated in front of a computer screen:

Color Stroop (Color-Word Interference) test [26]: For this task, participants completed a computerized, single-trial version of the task which involved the presentation of words corresponding to color names, printed in differently colored letters. They were asked to name the color of the letters while ignoring the printed word. The task consisted of 5, one-minute blocks in which stimulus presentation frequency varied from 2 to 1.25 seconds/word (blocks one and five: 2 seconds/word, blocks 2 and 4: 1.5 seconds/word, block 5: 1.25 seconds/word). During the first and last blocks, only congruent stimuli were presented, whereas the remaining blocks consisted of only incongruent stimuli. The Stroop task is commonly used as an anxiogenic stimulus in studies of autonomic nervous system function [27], [28], including in children with ASD [29].

Public speaking: For this task, participants delivered a 3 minute talk to 3 strangers. Public speaking tasks have been successfully used in previous studies examining cardiac responses to anxiogenic stimuli in neurotypical individuals [30], [31], [32] and in children with ASD [33], [34].

Each task was followed by a baseline condition where participants watched clips of animated movies. Baseline tasks were 5 minutes in duration. Previous studies have shown that movie watching is effective in returning heart rate data to baseline levels [7]. Prior to the experiment, participants watched a 15-minute movie clip to acclimate to the laboratory setting and sensors.

Measurements

Three-lead electrocardiogram (ECG) was measured using a wearable sensor from Shimmer Research. The ECG time-series, sampled at 256 Hz, was transmitted over BlueTooth to a laptop computer and stored. Analyses were carried out offline using Matlab. R-R intervals were extracted using a modified version of the algorithms presented in [35], [36]. In particular, the ECG signal was bandpass filtered between 5 and 15 Hz to maximize the QRS energy and to remove artifact noise, including baseline wandering, motion artifacts, and electrical noise. The signal was then differentiated, squared, and integrated using a 200 ms window. Peaks of the integrated signals were detected as R-waves using a detection threshold of 0.15 times the median of the past 10 beats and a blanking period of 200 ms. The RR sequence then underwent an outlier filtering algorithm which removed R-R values outside of acceptable limits. High and low limits were computed as 75% and 150% of the average of the median of all preceding beats and the median of 8 preceding beats. This combination was used to allow for adaptation to changes in median RR-interval over time.

Performance Evaluation

1) Performance Measure:

The performance of the algorithm was evaluated using classification sensitivity, specificity, and accuracy defined below:

$$\text{sensitivity} = \frac{TP}{TP + FN} \quad (15)$$

$$\text{specificity} = \frac{TN}{TN + FP} \quad (16)$$

$$\text{accuracy} = \frac{TP + TN}{TP + FN + TN + FP} \quad (17)$$

where true positives (TP) and false negatives (FN) are anxiety states that are correctly and incorrectly identified, respectively. True negatives (TN) and false positives (FP) are baseline states that are correctly and incorrectly identified, respectively. To highlight the trade-off between sensitivity and specificity, results are presented in the form of receiver operating characteristic (ROC) curves. The range $-10 < \tau < 10$ was used for generating these curves.

2) Ground Truth:

In order to calculate the above measures, a labeled ground truth set is needed. To obtain such a set, participants would need to provide self-reports of their arousal level throughout the experiment. This would require disengagement from the anxiogenic stimuli and as such would provide limited temporal resolution. Moreover, obtaining reliable self-reports of anxiety is a difficult task in the population of interest as ASD is associated with impairments in emotional awareness, introspection, and communication.

Due to the above challenges, self-reports were not used to generate the ground truth. Given that the anxiogenic stimuli used in this example study have been validated by several other studies [29], [33], [34], it was assumed that participants were in an arousal state when engaged in the Stroop and public speaking tasks. As such, data obtained during these two tasks are labeled as those belonging to an arousal class whereas data obtained during movie-watching were labeled as baseline. To ensure comparability of results among tasks, the last 3 minutes of each task were used for evaluation, except for the Stroop task where only the incongruent blocks were used (3 minutes). The filter was applied to the R-R record from the entire session and the state labels $\zeta_k$ associated with each measurement y(k) in the intervals of interest were used to compute sensitivity, specificity, and accuracy.

The performance sensitivity of the example disclosed system to its parameters was evaluated, based on the results of the example study, and the performance of the example system was compared to other methods.

Effect of Model Parameters

Figure 4A:
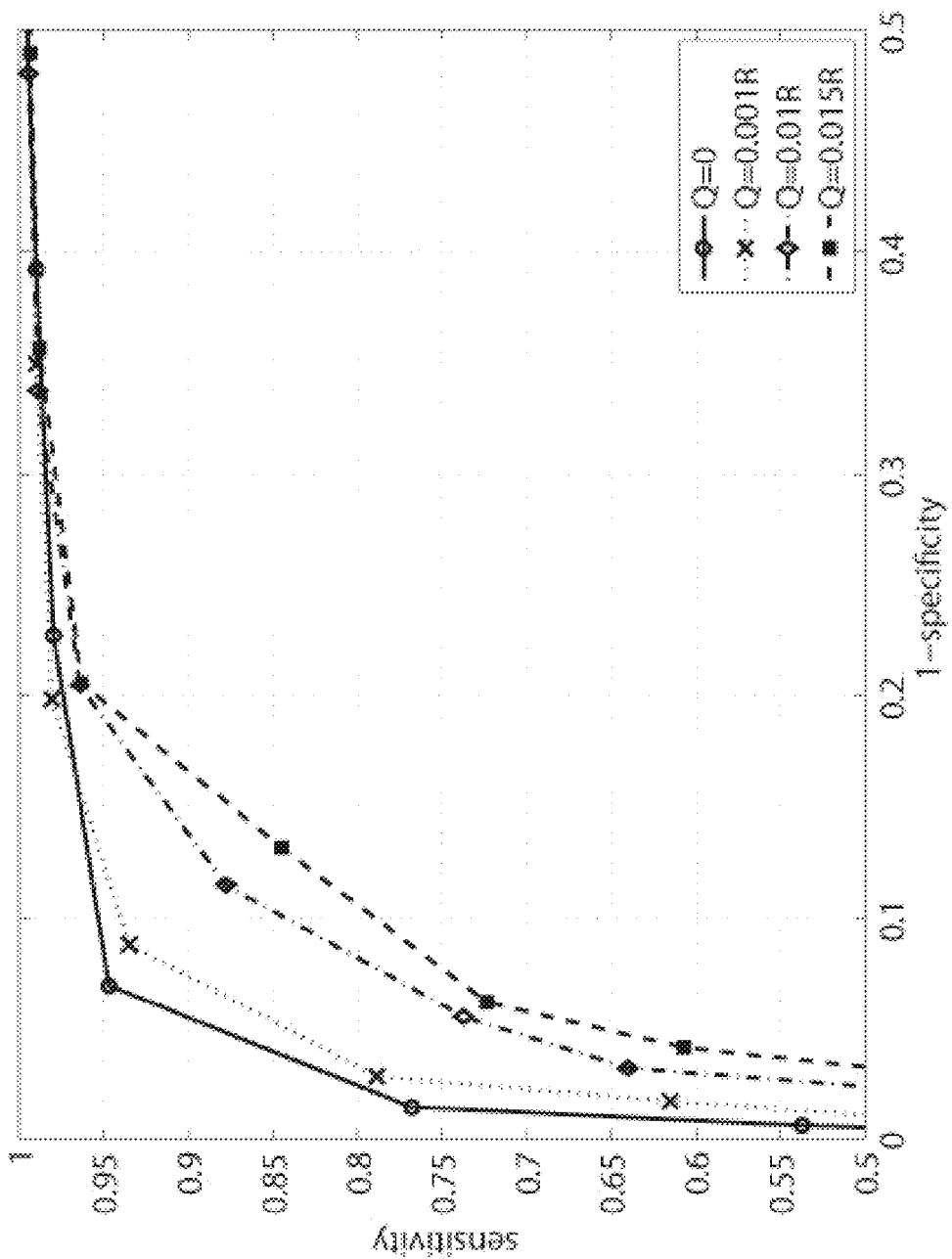
FIGS. 4a and 4b are charts illustrating the effect of noise covariance on the system performance of an example of the present disclosure.

The state-space model used in the example system (Equations (2) and (3)) requires specification of the noise covariances $Q_k$ and $\Sigma_k$. The measurements $\{y_k\}$ were used to estimate R(k) and determine Q(k)=M Σ(k). FIG. 4a shows an example effect of changing the ratio of the noise covariances M on system performance of the example system. The optimal performance was found to be obtained for M=0.

Figure 4B:
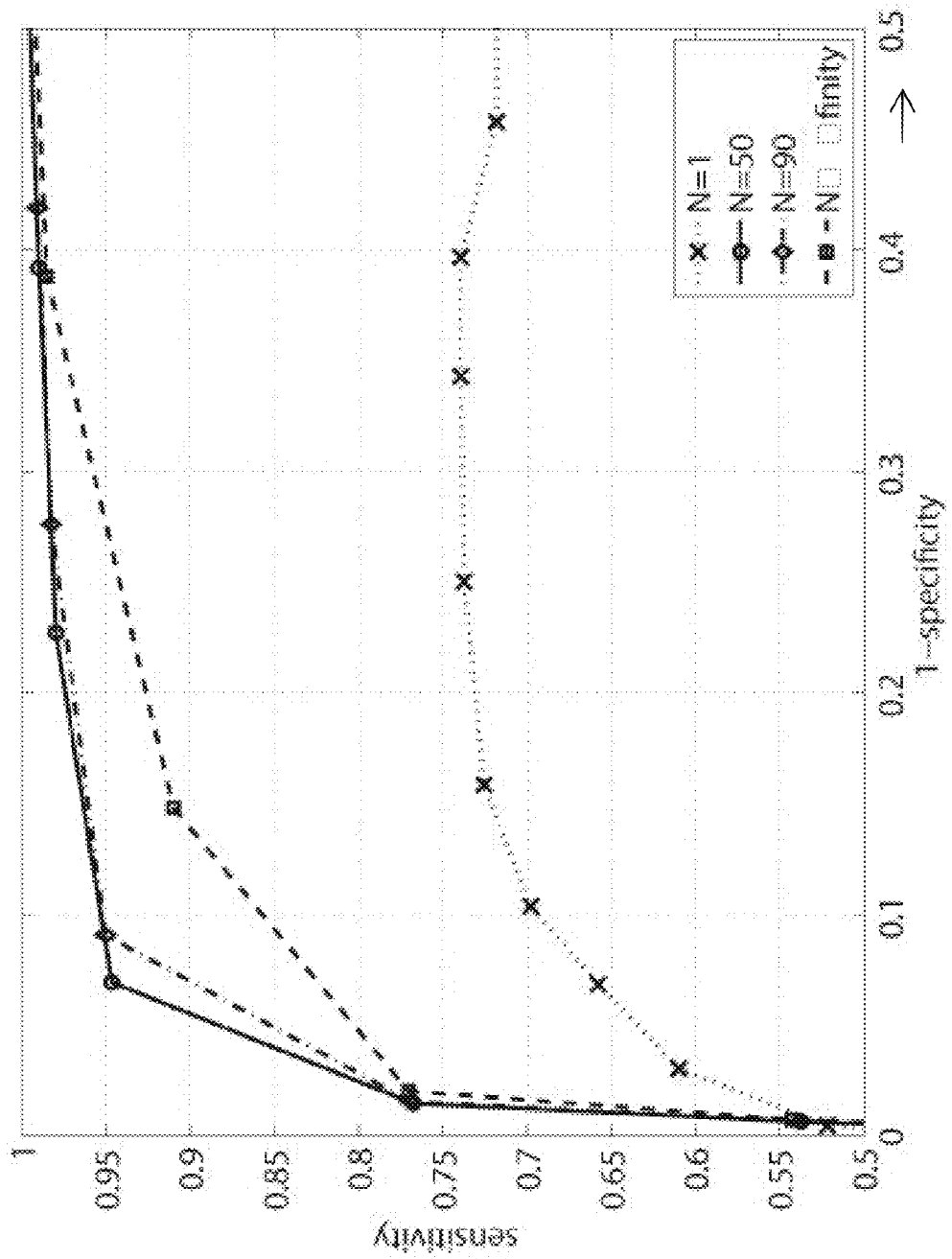

Next, the effect of the parameter N on system performance was examined (see FIG. 4b). This parameter governs the fading out of the measurements from refinement of the state estimate during arousal states and is used to mimic a multiple model filtering approach. Fading out of measurements may be implemented as a lesser weighting being given to the measurements, as compared to the weighting given to the measurements during baseline states. For N=1, measurements during arousal states are not faded out, that is they are given full weighting equal to the weighting given to measurements during baseline states. For N→∞, measurements during arousal states are entirely faded out (i.e., ignored), that is they are given weighting of zero. In between these two cases, measurements during arousal states are partially faded out, that is they are given a weighting that is non-zero but is less than the weighting given to measurements during baseline states. As seen in FIG. 4b, the optimal system performance was found to be achieved for values of N in the range 50-75.

Effect of Detection Threshold

Figure 5:
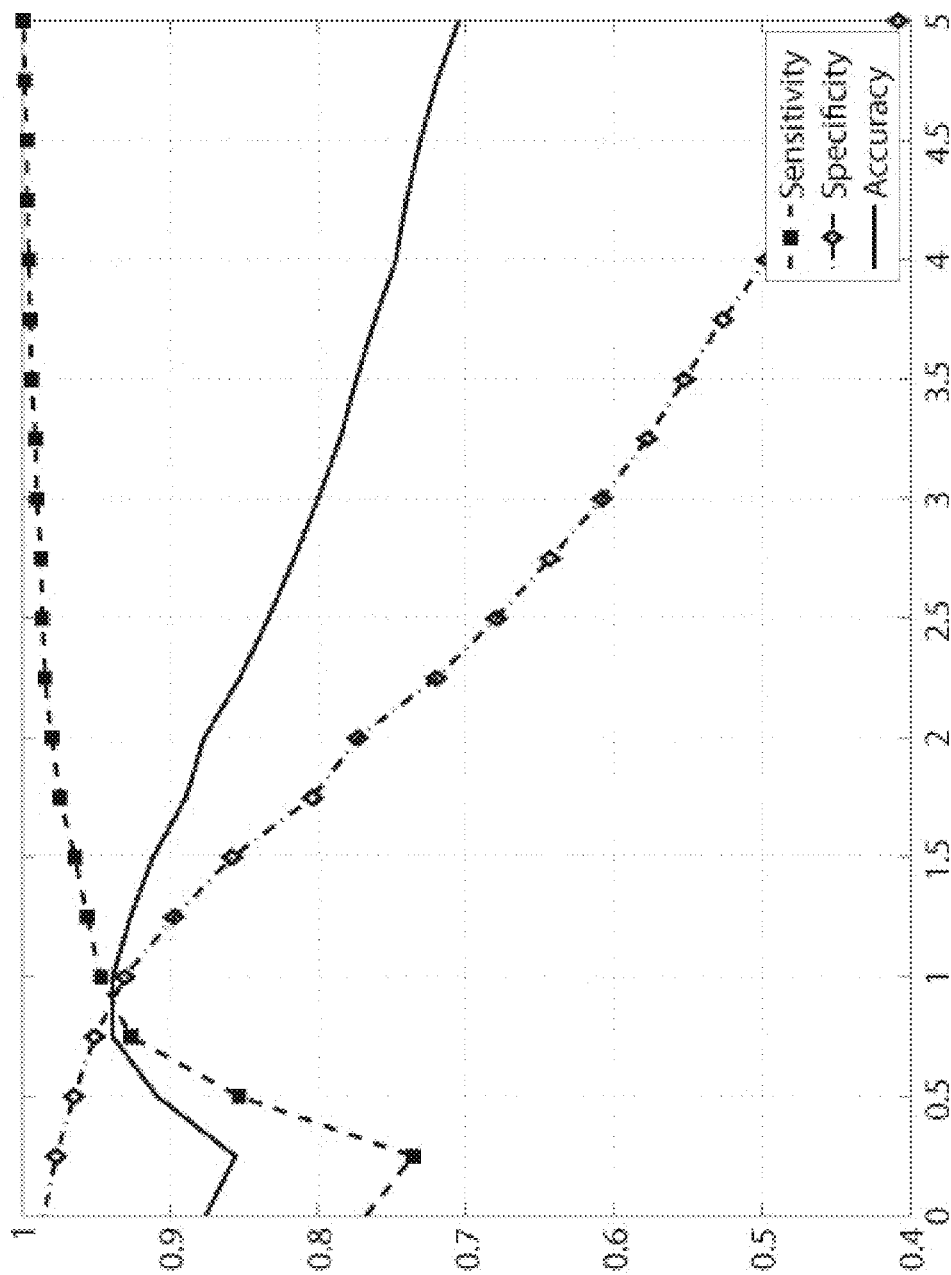
FIG. 5 is a chart illustrating the effect of detection threshold on the system performance of an example of the present disclosure.

The threshold τ is used to detect arousal states given the residual record from the modified Kalman filter. FIG. 5 shows the effect of this parameter on system performance. The range 0.5<τ<1.5 was found to result in optimal system accuracy in this example.

Effect of Trend Parameters

Figure 6A:
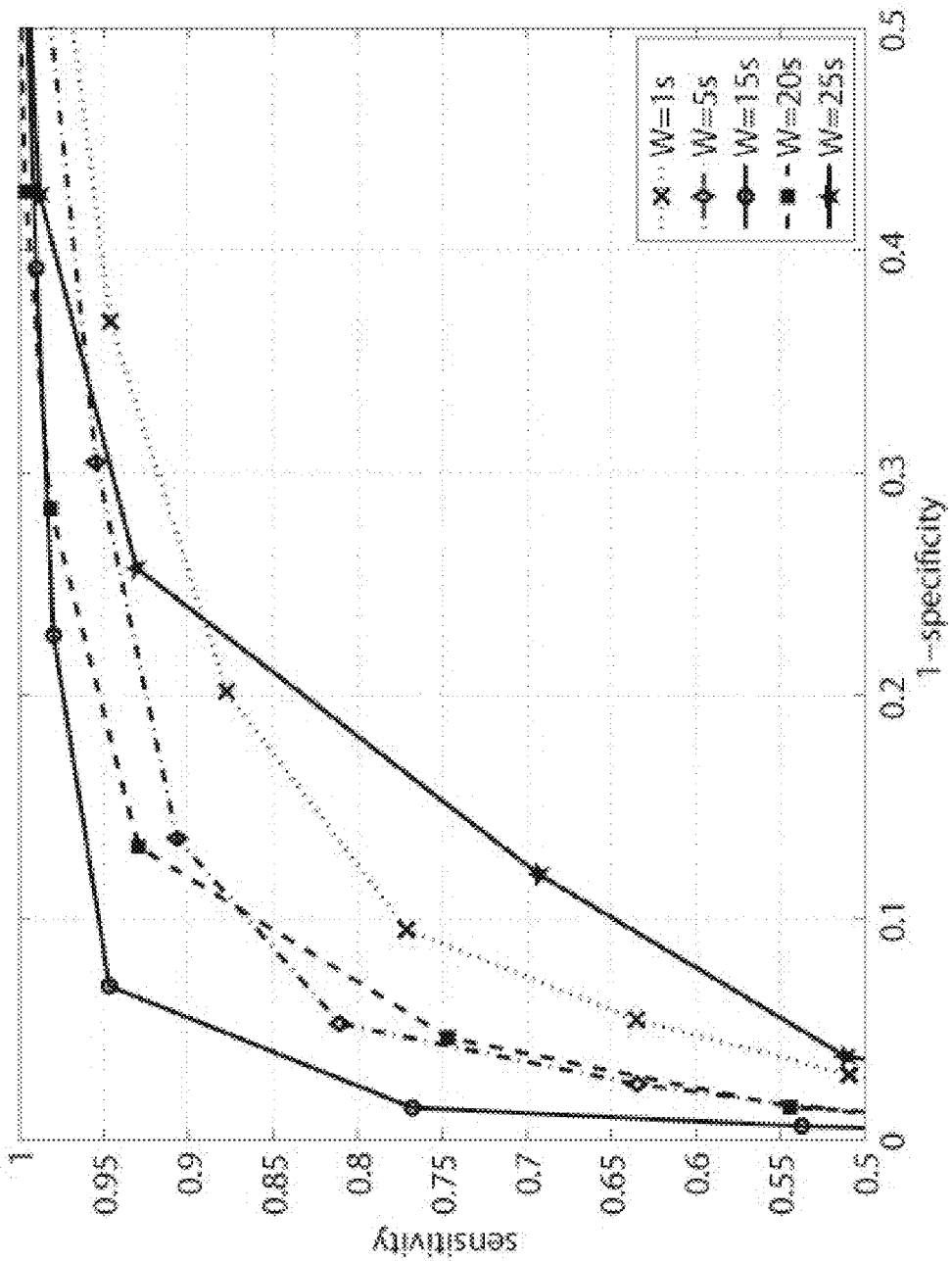
FIGS. 6a and 6b are charts illustrating the effect of trend calculation parameters on the system performance of an example of the present disclosure.
Figure 6B:
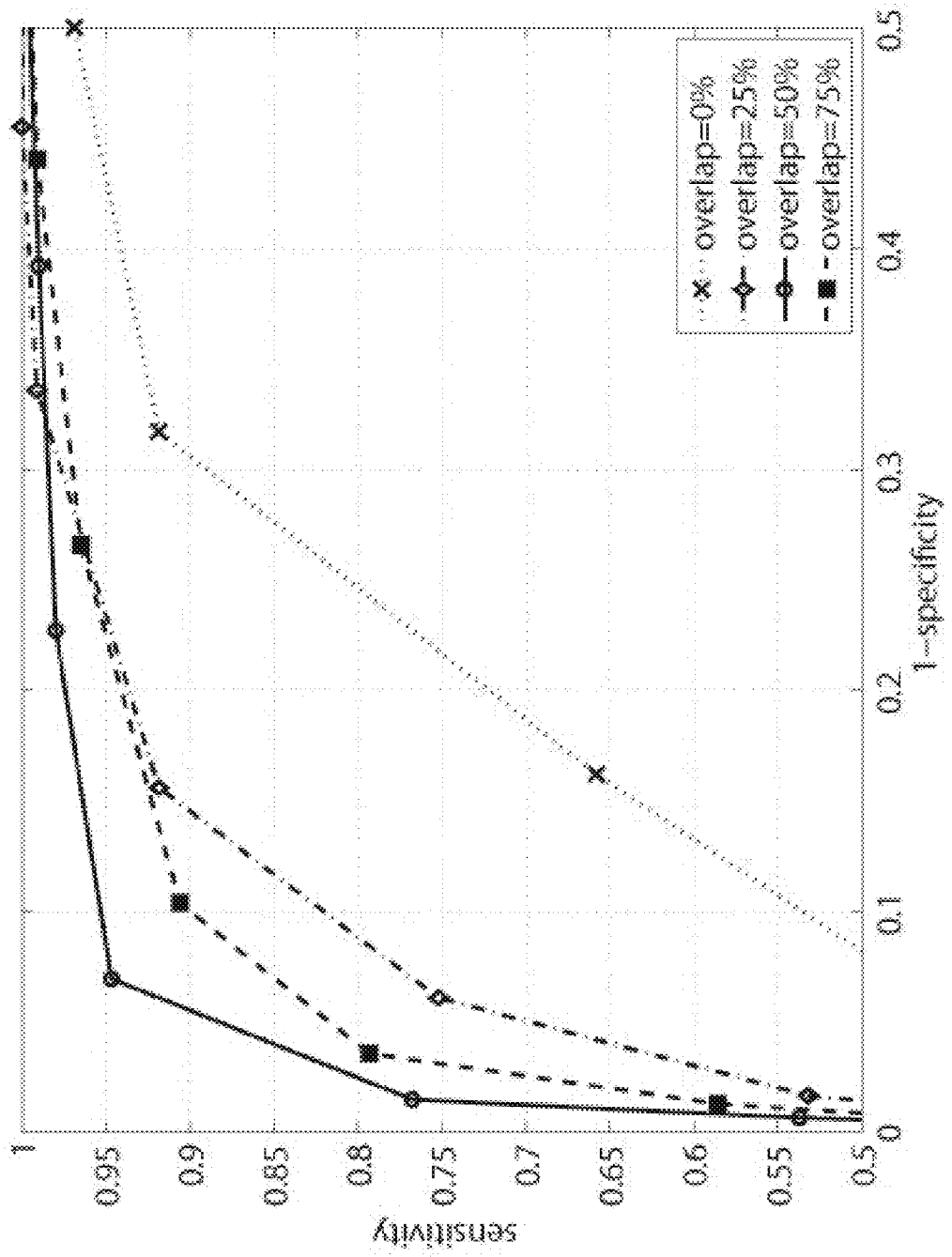

FIGS. 6a and 6b show the effect of the parameters used for generating the slowly varying R-R trend as input to the Kalman filter (window length W and overlap). A window length of 15 seconds with 50% overlap was found to provide the optimal performance.

Residual Computation

Figure 7:
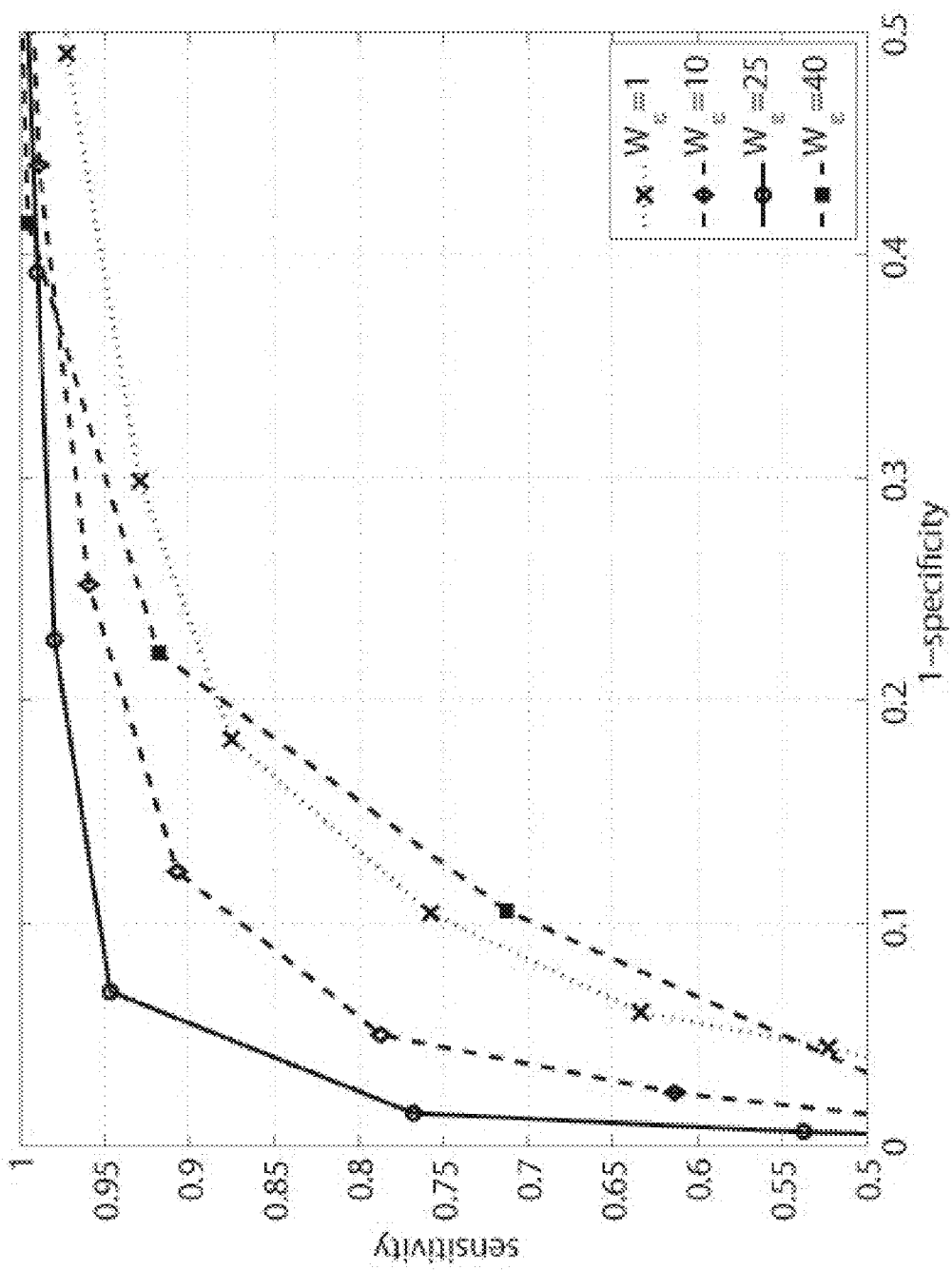
FIG. 7 is a chart illustrating the effect of the smoothing window length on the system performance of an example of the present disclosure.

To detect arousal, long-term and short-term sample mean and variance of the residual sequence are compared. FIG. 7 shows how the length of the estimation window $W_\epsilon$ affects system performance. As seen, $W_\epsilon=25$ was found to provide the best system performance.

Comparison to Other Methods

In various examples, the present disclosure describes a Kalman filtering framework for detection of anxiety-related cardiac changes. Through manipulation of the measurement noise covariance, the example disclosed system affects the contribution of measurements obtained during arousal states to the final system estimates. In this section, the performances of three cases of the Kalman filtering frameworks are described, namely, the traditional Kalman filter adapted from [13] for tracking of normal rhythms (N=1), Kalman filtering with missing observations [16] (N→∞), and the approach used in the example disclosed system (1<N<∞).

Currently, no other unsupervised online algorithms for physiological detection of arousal have been proposed. The performance of the disclosed methods and systems is discussed below with reference to two other algorithms, in order to illustrate some features of the disclosed methods and systems compared with conventional approaches.

Conventional fixed baseline model: In this approach, mean μ and standard deviation σ of baseline R-R sequence are computed from a 10-sample baseline R-R sequence. The detection algorithm then detects an anxiety state if y(k)<μ−τσ. This approach mimics the situation where the baseline model is assumed to be time-invariant (e.g., as in supervised techniques). Comparison to this technique highlights the advantages of using a time-varying baseline model.

Conventional sliding window baseline model: This approach is similar to the fixed baseline model which the exception that the mean μ and standard deviation σ of baseline R-R sequence are computed from a sliding window for every measurement y(k). A difference between this approach and the technique of the present disclosure is that a priori knowledge about the system not incorporated in this conventional approach. Comparison to this technique illustrates the advantage of using the state-space model for characterizing baseline activity.

Figure 8:
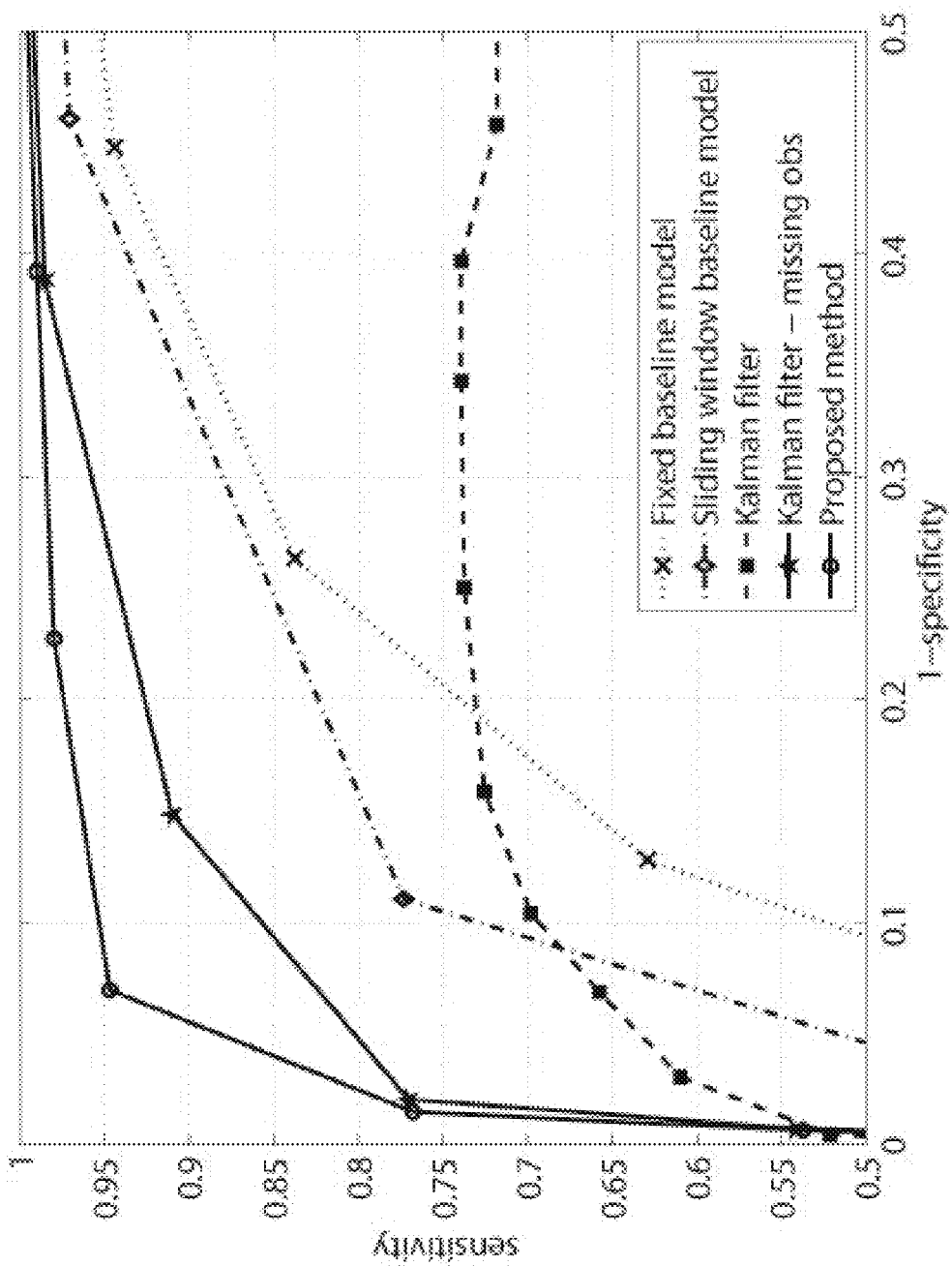
FIG. 8 is a chart comparing the sensitivity of different detection models, compared to an example of the present disclosure.

FIG. 8 shows the ROC curves for the five methods and the optimal accuracy for each method is reported in Table II. As seen, the disclosed method with 1<N<∞ was found to provide the best performance, followed by the disclosed method with N→∞, the sliding window method, and the fixed baseline model. Traditional Kalman filtering was found to result in the poorest performance among the five methods.

TABLE II

|  | Sensitivity | Specificity | Accuracy |
| --- | --- | --- | --- |
| Fixed baseline model | 0.84 | 0.74 | 0.79 |
| Sliding window baseline model | 0.77 | 0.89 | 0.83 |
| Traditional Kalman filter | 0.70 | 0.90 | 0.80 |
| Modified Kalman filter-missing observations | 0.91 | 0.95 | 0.88 |
| Example disclosed method | 0.95 | 0.93 | 0.94 |

In various examples, the present disclosure provides a Kalman filtering framework for automatic detection of anxiety-related cardiac changes. At the core of the Kalman filter is a state-space model which specifies the a priori knowledge about system dynamics. Results from example studies showed that the performance of the example disclosed system may be affected by the choice of state-space model parameters. In particular, system performance was found to be sensitive to the choice of the noise covariances $Q_k$ and $R_k$ which specify the uncertainty associated with the system and measurement models, respectively. They affect the Kalman filter estimate as $\hat{x}_{k+1|k+1}$ is a linear combination of the prediction $\hat{x}_{k+1|k}$ and the measurement $y_k$ where the weights are controlled by the noise covariances $Q_k$ and $R_k$. Results from example studies show that better performance is achieved with the choice of Q=0, which is a degenerate case corresponding to a system model with no uncertainty. This is consistent with the assumption of a constant baseline model and the model proposed in [13] for R-R intervals.

In the disclosed system, the measurement covariance $R_k$ is manipulated to mimic a multiple model system. When the system is in an arousal state, the effect of the measurements is "faded out" (i.e., given less weighting or entirely ignored) as they are no longer concordant with the baseline model. Results from example studies show that this fading improves the performance of the system. The degree of fading, specified by the parameter N, was also found to affect performance. Specifically, total fading of measurements (i.e., totally ignoring measurements during arousal states) was found to be a suboptimal approach. Two reasons may contribute to this. First, recall that the proposed system uses feedback to adjust R(k) using state choices ζ(k−1). As such, detection errors propagate back to the system and affect the choice of R(k). Complete fading out of measurements (i.e., N→∞) does not allow recovery from such errors whereas partial measurement fading allows the system to slowly readjust its state estimates using incoming measurements. Results from example studies showed that the system performance is relatively insensitive to the choice of N in that a large range of values lead to near-optimal performance.

System performance may also be affected by parameters used for generating the measurements y(k) from the R-R sequence. The disclosed examples use a slowly-varying R-R trend generated as a moving average of the R-R sequence extracted from the ECG record. Results from example studies revealed a trade-off between smoothing the R-R intervals to remove high-frequency variability and over-smoothing the arousal-related changes in the R-R signal. The latter are expected to be in the frequency range below that of spontaneous breathing (i.e., <1 Hz).

Results from example studies showed that the detection threshold affects system accuracy. Anxiety-related arousal is generally associated with a decrease in R-R intervals [7]. As such, it may be expected that the filter residual are negative in anxiety states, leading to a negative threshold τ. However, results from example studies indicate that optimal system performance is obtained for 0.5<τ<1.5. This may reflect a skewed residual distribution resulting from the relative infrequency of arousal in the data used in the example studies.

Overall, results from example studies show that the example disclosed method can detect physiological arousal associated with anxiety with relatively high accuracy, providing support for technical feasibility of augmenting anxiety treatments with automatic detection techniques. The data used for system validation in the example studies were collected under controlled laboratory settings.

For use in naturalistic settings, several additional technical aspects should be considered. For example, in the example studies described above, differentiation of baseline from arousal was addressed. However, other mental, cognitive, and affective processes are known to affect cardiac activity. In some examples, the present disclosure may include implementation of filters or other algorithms for differentiation of arousal related to these processes from that related to anxiety. Additional algorithms or filters may also be implemented to avoid interference from environmental noise, for example.

Applications

The present disclosure may be useful for detection of anxiety in subjects who may be prone to anxiety and who may have low self-awareness or have an inability to express their anxiety level. For example, the present disclosure may be useful for detection of anxiety in subjects with ASD.

Because the present disclosure may be implemented using wearable physiological sensors and portable electronic devices (e.g., smartphones), the present disclosure may enable detection of anxiety in the subject's natural settings and normal day-to-day activities. Such a system may also be more readily accepted by the subject and more socially acceptable (as compared to wired sensors typically used in a lab setting), because of the ubiquity of portable electronic devices in day-to-day activities. This may enable better understanding of anxiety triggers in real-life situations, better identification of biological drivers of behavior, better measurement of contextual factors related to anxiety and/or better understanding of personal and environmental factors that affect ASD symptoms.

The present disclosure may help to promote self-awareness and self-relaxation by the subject. By presenting the subject with real-time feedback and optionally tailored relaxation guidance, the present disclosure may help to teach children with ASD navigate social situations in a personalized way. The guidance provided may be personalized based on the effectiveness for a given subject, and may be complementary to the subject's other ASD treatments. The guidance and treatment may be better integrated into the subject's daily living.

The embodiments of the present disclosure described above are intended to be examples only. The present disclosure may be embodied in other specific forms. Alterations, modifications and variations to the disclosure may be made without departing from the intended scope of the present disclosure. While the systems, devices and processes disclosed and shown herein may comprise a specific number of elements/components, the systems, devices and assemblies could be modified to include additional or fewer of such elements/components. For example, while any of the elements/components disclosed may be referenced as being singular, the embodiments disclosed herein could be modified to include a plurality of such elements/components. Selected features from one or more of the above-described embodiments may be combined to create alternative embodiments not explicitly described. All values and subranges within disclosed ranges are also disclosed. The subject matter described herein intends to cover and embrace all suitable changes in technology. All references mentioned are hereby incorporated by reference in their entirety.

REFERENCES

[1] D. H. Barlow, "Unraveling the mysteries of anxiety and its disorders from the perspective of emotion theory." *American Psychologist*, vol. 55, no. 11, pp. 1247-1263, 2000.

[2] J. Zhai and A. Barreto, "Stress detection in computer users based on digital signal processing of noninvasive physiological variables," in *Engineering in Medicine and Biology Society, 2006. EMBS '06. 28th Annual International Conference of the IEEE*. IEEE, 2006, pp. 1355-1358.

[3] J. A. Healey and R. W. Picard, "Detecting stress during real-world driving tasks using physiological sensors," *Intelligent Transportation Systems, IEEE Transactions on*, vol. 6, no. 2, pp. 156-166, 2005.

[4] A. de Santos Sierra, C. S. A'vila, J. Guerra Casanova, and G. B. del Pozo, "A stress-detection system based on physiological signals and fuzzy logic," *Industrial Electronics, IEEE Transactions on*, vol. 58, no. 10, pp. 4857-4865, 2011.

[5] M. J. Skinner and P. A. Simpson, "Workload issues in military tactical airlift," *The International Journal of Aviation Psychology*, vol. 12, no. 1, pp. 79-93, 2002.

[6] F.-T. Sun, C. Kuo, H.-T. Cheng, S. Buthpitiya, P. Collins, and M. Griss, "Activity-aware mental stress detection using physiological sensors," in *Mobile Computing, Applications, and Services*. Springer, 2012, pp. 211-230.

[7] A. Kushki, E. Drumm, M. P. Mobarak, N. Tanel, A. Dupuis, T. Chau, and E. Anagnostou, "Investigating the autonomic nervous system response to anxiety in children with autism spectrum disorders," *PLoS one*, vol. 8, no. 4, p. e59730, 2013.

[8] P. J. Lang, "Fear reduction and fear behavior: Problems in treating a construct." in *Research in Psychotherapy Conference*, 3rd, May-Jun., 1966, Chicago, Ill., US. American Psychological Association, 1968, pp. 90-102.

[9] D. Robertson, I. Biaggioni, G. Burnstock, P. A. Low, and J. F. Paton, *Primer on the autonomic nervous system*. Access Online via Elsevier, 2011.

[10] A. Camm, M. Malik, J. Bigger, G. Breithardt, S. Cerutti, R. Cohen, P. Coumel, E. Fallen, H. Kennedy, R. Kleiger et al., "Heart rate variability: standards of measurement, physiological interpretation and clinical use. task force of the european society of cardiology and the north american society of pacing and electrophysiology," *Circulation*, vol. 93, no. 5, pp. 1043-1065, 1996.

[11] Y. Bar-Shalom, X. R. Li, and T. Kirubarajan, *Estimation with applications to tracking and navigation: theory algorithms and software*. John Wiley & Sons, 2004.

[12] O. L. do Valle Costa, M. D. Fragoso, and R. P. Marques, *Discrete-time Markov jump linear systems*. Springer, 2006.

[13] D. E. Gustafson, A. S. Willsky, I.-Y. Wang, M. C. Lancaster, and J. H. Triebwasser, "Ecg/vcg rhythm diagnosis using statistical signal analysis-i. identification of persistent rhythms," *Biomedical Engineering, IEEE Transactions on*, no. 4, pp. 344-353, 1978.

[14] D. F. Sittig and K.-H. Cheung, "A parallel implementation of a multi-state kalman filtering algorithm to detect ecg arrhythmias," *International journal of clinical monitoring and computing*, vol. 9, no. 1, pp. 13-22, 1992.

[15] J. McNames and M. Aboy, "Statistical modeling of cardiovascular signals and parameter estimation based on the extended kalman filter," *Biomedical Engineering, IEEE Transactions on*, vol. 55, no. 1, pp. 119-129, 2008.

[16] B. Sinopoli, L. Schenato, M. Franceschetti, K. Poolla, M. I. Jordan, and S. S. Sastry, "Kalman filtering with intermittent observations," *Automatic Control, IEEE Transactions on*, vol. 49, no. 9, pp. 1453-1464, 2004.

[17] S. White, D. Oswald, T. Ollendick, and L. Scahill, "Anxiety in children and adolescents with autism spectrum disorders," *Clinical Psychology Review*, vol. 29, no. 3, pp. 216-229, 2009.

[18] B. MacNeil, V. Lopes, and P. Minnes, "Anxiety in children and adolescents with Autism Spectrum Disorders," *Research in Autism Spectrum Disorders*, vol. 3, no. 1, pp. 1-21, 2009.

[19] J. Reaven, "Children with high-functioning autism spectrum disorders and co-occurring anxiety symptoms: Implications for assessment and treatment," *Journal for Specialists in Pediatric Nursing*, vol. 14, no. 3, pp. 192-199, 2009.

[20] D. Sukhodolsky, L. Scahill, K. Gadow, L. Arnold, M. Aman, C. McDougle, J. McCracken, E. Tierney, S. Williams White, L. Lecavalier et al., "Parent-rated anxiety symptoms in children with pervasive developmental disorders: Frequency and association with core autism symptoms and cognitive functioning," *Journal of Abnormal Child Psychology*, vol. 36, no. 1, pp. 117-128, 2008.

[21] A. Blakeley-Smith, J. Reaven, K. Ridge, and S. Hepburn, "Parent-child agreement of anxiety symptoms in youth with autism spectrum disorders," *Research in Autism Spectrum Disorders*, vol. 6, no. 2, pp. 707-716, 2012.

[22] A. Kushki, J. Brian, T. Dupuis A, and A. E, "Functional autonomic nervous system profile in children with asd," *Molecular Autism*, Submitted 2014.

[23] C. Lord, S. Risi, L. Lambrecht, E. Cook, B. Leventhal, P. DiLavore, A. Pickles, and M. Rutter, "The autism diagnostic observation schedulegeneric: A standard measure of social and communication deficits associated with the spectrum of autism," *Journal of autism and developmental disorders*, vol. 30, no. 3, pp. 205-223, 2000.

[24] C. Lord, M. Rutter, and A. Le Couteur, "Autism diagnostic interview-revised: a revised version of a diagnostic interview for caregivers of individuals with possible pervasive developmental disorders," *Journal of autism and developmental disorders*, vol. 24, no. 5, pp. 659-685, 1994.

[25] C. Ebesutani, A. Bernstein, B. J. Nakamura, B. F. Chorpita, and J. R. Weisz, "A psychometric analysis of the revised child anxiety and depression scale-parent version in a clinical sample," *Journal of abnormal child psychology*, vol. 38, no. 2, pp. 249-260, 2010.

[26] J. Stroop, "Studies of interference in serial verbal reactions." *Journal of Experimental Psychology*, vol. 18, no. 6, pp. 643-662, 1935.

[27] M. Fechir, M. Gamer, I. Blasius, T. Bauermann, M. Breimhorst, P. Schlindwein, T. Schlereth, and F. Birklein, "Functional imaging of sympathetic activation during mental stress," *Neuroimage*, vol. 50, no. 2, pp. 847-854, 2010.

[28] Y. Boutcher and S. Boutcher, "Cardiovascular response to stroop: effect of verbal response and task difficulty," *Biological psychology*, vol. 73, no. 3, pp. 235-241, 2006.

[29] A. Kushki, E. Drumm, M. P. Mobarak, N. Tanel, A. Dupuis, T. Chau, and E. Anagnostou, "Investigating the autonomic nervous system response to anxiety in children with autism spectrum disorders," *PloS one*, vol. 8, no. 4, p. e59730, 2013.

[30] L. W. Carlile et al., "Special reports: Heart rate as an index of speech anxiety." *Speech Monographs*, vol. 38, no. 1, pp. 65-9, 1971.

[31] M. J. Beatty and R. R. Behnke, "Effects of public speaking trait anxiety and intensity of speaking task on heart rate during performance," *Human Communication Research*, vol. 18, no. 2, pp. 147-176, 1991.

[32] M. Po rho la, "Arousal styles during public speaking," *Communication Education*, vol. 51, no. 4, pp. 420-438, 2002.

[33] L. Jansen, C. Gispen-De Wied, R. Van Der Gaag, and H. Van Engeland, "Differentiation between autism and multiple complex developmental disorder in response to psychosocial stress," *Neuropsychopharmacology*, vol. 28, no. 3, pp. 582-590, 2003.

[34] T. Levine, C. Dhossche, C. Ross, L. Stoppelbein, J. Charles, C. Harrison, H. Britt, A. Estes, V. Hus, L. Elder et al., "Physiologic arousal to social stress in children with autism spectrum disorders: A pilot study," *Research in Autism Spectrum Disorders*, vol. 6, no. 1, pp. 177-183, 2012.

[35] J. Pan and W. J. Tompkins, "A real-time qrs detection algorithm," *Biomedical Engineering, IEEE Transactions on*, no. 3, pp. 230-236, 1985.

[36] P. S. Hamilton and W. J. Tompkins, "Quantitative investigation of qrs detection rules using the mit/bih arrhythmia database," *Biomedical Engineering, IEEE Transactions on*, no. 12, pp. 1157-1165, 1986.

[37] Lang R, Regester A, Lauderdale S, Ashbaugh K, Haring A (2010) Treatment of anxiety in autism spectrum disorders using cognitive behaviour therapy: A systematic review. Developmental Neurorehabilitation 13: 53-63.

[38] Gillott A, Furniss F, Walter A (2001) Anxiety in high-functioning children with autism. Autism 5: 277-286.

[39] White S, Roberson-Nay R (2009) Anxiety, social deficits, and loneliness in youth with autism spectrum disorders. Journal of autism and developmental disorders 39:1006-1013.

[40] Farrugia S, Hudson J (2006) Anxiety in adolescents with Asperger syndrome: Negative thoughts, behavioral problems, and life interference. Focus on Autism and Other Developmental Disabilities 21: 25-35.

[41] Kim J, Szatmari P, Bryson S, Streiner D, Wilson F (2000) The prevalence of anxiety and mood problems among children with autism and Asperger syndrome. Autism 4: 117-132.

[42] Helverschou S, Martinsen H (2011) Anxiety in people diagnosed with autism and intellectual disability: Recognition and phenomenology. Research in Autism Spectrum Disorders 5: 377-387.

[43] Amaral D, Corbett B (2003) The amygdala, autism and anxiety. In: Novartis Foundation symposium. volume 251, p. 177.

[44] Franchini K G, Cowley A W (2011) Autonomic control of cardiac function. In: Robertson D, Biaggioni I, Burnstock G, Low P, Paton J, editors, Primer on the autonomic nervous system, Academic Press. 134-138.

[45] Dawson M, Schell A, Filion D (2000) The electrodermal system. In: Cacioppo J, Tassinary L G, Berntson G G, editors, Handbook of psychophysiology, (Cambridge University Press). 200-223.

[46] Vetrugno R, Liguori R, Cortelli P, Montagna P (2003) Sympathetic skin response. Clinical autonomic research 13: 256-270.

[47] Franchini K G, Cowley A W (2011) Neurogenic control of blood vessels. In: Robertson D, Biaggioni I, Burnstock G, Low P, Paton J, editors, Primer on the autonomic nervous system, Academic Press. 139-143.

[48] Kistler A, Mariauzouls C, von Berlepsch K (1998) Fingertip temperature as an indicator for sympathetic responses. International Journal of Psychophysiology 29: 35-41.

[49] Stroop J (1935) Studies of interference in serial verbal reactions. Journal of Experimental Psychology 18: 643-662.

[50] Toichi M, Kamio Y (2003) Paradoxical autonomic response to mental tasks in autism. Journal of autism and developmental disorders 33: 417-426.

[51] Ming X, Julu P, Brimacombe M, Connor S, Daniels M (2005) Reduced cardiac parasympathetic activity in children with autism. Brain and Development 27: 509-516.

[52] Van Hecke A, Lebow J, Bal E, Lamb D, Harden E, et al. (2009) Electroencephalogram and heart rate regulation to familiar and unfamiliar people in children with autism spectrum disorders. Child development 80: 1118-1133.

[53] Bal E, Harden E, Lamb D, Van Hecke A, Denver J, et al. (2010) Emotion recognition in children with autism spectrum disorders: Relations to eye gaze and autonomic state. Journal of autism and developmental disorders 40: 358-370.

[54] Yang T, Simmons A, Matthews S, Tapert S, Bischoff-Grethe A, et al. (2007) Increased amygdale activation is related to heart rate during emotion processing in adolescent subjects. Neuroscience letters 428: 109-114.

[55] Thayer J, Sternberg E (2006) Beyond heart rate variability. Annals of the New York Academy of Sciences 1088: 361-372.

[56] Mosconi M, Cody-Hazlett H, Poe M, Gerig G, Gimpel-Smith R, et al. (2009) Longitudinal study of amygdala volume and joint attention in 2-to 4-year-old children with autism. Archives of general psychiatry 66: 509.

[57] Juranek J, Filipek P, Berenji G, Modahl C, Osann K, et al. (2006) Association between amygdale volume and anxiety level: magnetic resonance imaging (mri) study in autistic children. Journal of child neurology 21: 1051-1058.

[58] Kleinhans N, Richards T, Weaver K, Johnson L, Greenson J, et al. (2010) Association between amygdala response to emotional faces and social anxiety in autism spectrum disorders. Neuropsychologia 48: 3665-3670.

[59] Porges S (2003) The polyvagal theory: Phylogenetic contributions to social behavior. Physiology & Behavior 79: 503-513.

[60] Haznedar M, Buchsbaum M, Wei T, Hof P, Cartwright C, et al. (2000) Limbic circuitry in patients with autism spectrum disorders studied with positron emission tomography and magnetic resonance imaging. American Journal of Psychiatry 157: 1994-2001.

[61] Coull, J., Frith, C., Frackowiak, R. S. J., Grasby, P.: A fronto-parietal network for rapid visual information processing: a pet study of sustained attention and working memory. Neuropsychologia 34(11), 1085-1095 (1996).

[62] McAuley, T., Crosbie, J., Charach, A., Schachar, R.: The persistence of cognitive deficits in remitted and unremitted adhd: a case for the state-independence of response inhibition. Journal of Child Psychology and Psychiatry (2013).

[63] Verbruggen, F., Logan, G. D.: Models of response inhibition in the stop-signal and stop-change paradigms. Neuroscience & Biobehavioral Reviews 33(5), 647-661 (2009)

[64] Baron-Cohen, S., Wheelwright, S., Hill, J., Raste, Y., Plumb, I.: The reading the mind in the eyes test revised version: A study with normal adults, and adults with asperger syndrome or high-functioning autism. Journal of Child Psychology and Psychiatry 42(2), 241-251 (2001).

[65] Jansen, L. M. C., Gispen-de Wied, C. C., Wiegant, V. M., Westenberg, H. G. M., Lahuis, B. E., van Engeland, H.: Autonomic and neuroendocrine responses to a psychosocial stressor in adults with autistic spectrum disorder. Journal of autism and developmental disorders 36(7), 891-899 (2006).

[66] Smeekens, I., Didden, R., Verhoeven, E.: Exploring the relationship of autonomic and endocrine activity with social functioning in adults with autism spectrum disorders. Journal of autism and developmental disorders, 1-11 (2013)

[67] Russell, E., Sofronoff, K., Russell, E., Sofronoff, K.: Anxiety and social worries in children with asperger syndrome. Australian and New Zealand Journal of Psychiatry 39(7), 633-638 (2005).

[68] Kerns, C. M., Kendall, P. C.: The presentation and classification of anxiety in autism spectrum disorder. Clinical Psychology: Science and Practice 19(4), 323-347 (2012).

[69] Porges, S. W.: The Polyvagal Theory: Neurophysiological Foundations of Emotions, Attachment, Communication, and Self-regulation. WW Norton & Company, New York; London (2011).

[70] Baron-Cohen, S., Ring, H. A., Wheelwright, S., Bullmore, E. T., Brammer, M. J., Simmons, A., Williams, S. C.: Social intelligence in the normal and autistic brain: an fmri study. European Journal of Neuroscience 11(6), 1891-1898 (1999).

The invention claimed is:

1. A system for detection of anxiety in a subject, the system comprising:
an output device for providing feedback about presence of absence of anxiety to the subject or another party;
a processor coupled to the output device, the processor being configured to:
receive at least one physiological signal, from one or more sensors coupled to the processor, that is relevant to a measurement of anxiety;
extract at least one feature from the at least one physiological signal, wherein the at least one extracted feature has a value that is affected by the subject's anxiety level;
process the at least one extracted feature using a modified Kalman filter, the modified Kalman filter being modified to update a state model using a first weighting of the at least one extracted feature when the at least one extracted feature has a value within a predicted noise model, and to update the state model using a second weighting of the at least one extracted feature when the at least one extracted feature has a value outside of the predicted noise model, the second weighting being less than the first weighting; and provide one or more output signals to the output device to cause the output device to indicate presence of anxiety when the at least one extracted feature has a value outside of the predicted noise model.

2. The system of claim 1 further comprising one or more sensors for detecting physiological signals.

3. The system of claim 1 wherein the output device is a display screen and the feedback is provided as a visual indicator of the subject's anxiety level.

4. The system of claim 1 wherein the system is implemented in a portable electronic device.

5. The system of claim 4 wherein the portable electronic device is a wearable electronic device.

6. The system of claim 1 wherein the at least one physiological signal comprises at least a cardiac signal.

7. The system of claim 1 wherein the processor is further configured to provide one or more output signals to the output device to cause the output device to indicate absence of anxiety when the at least one extracted feature has a value within the predicted noise model.

8. A method, implemented in an electronic device, for detecting anxiety in a subject, the method comprising:

receiving, from one or more sensors coupled to the electronic device, at least one physiological signal from the subject that is relevant to a measurement of anxiety;

extracting at least one feature from the at least one physiological signal, wherein the extracted feature has a value that is affected by the subject's anxiety level;

processing the at least one extracted feature using a modified Kalman filter, the modified Kalman filter being modified to update a state model using a first weighting of the at least one extracted feature when the at least one extracted feature has a value within a predicted noise model, and to update the state model using a second weighting of the at least one extracted feature when the at least one extracted feature has a value outside of the predicted noise model, the second weighting being less than the first weighting; and providing one or more output signals to an output device of the electronic device to cause the output device to indicate presence of anxiety when the at least one extracted feature has a value outside of the predicted noise model.

9. The method of claim 8 further comprising providing feedback about presence or absence of anxiety to the subject or another party by transmitting the one or more output signals to the output device to cause the feedback to be provided to the subject or the other party.

10. The method of claim 8 wherein the output device is a display screen and the feedback is provided as a visual indicator of the subject's anxiety level.

11. The method of claim 8 wherein the output device is implemented in a portable electronic device.

12. The method of claim 11 wherein the portable electronic device is a wearable electronic device.

13. The method of claim 8 wherein the at least one physiological signal comprises at least a cardiac signal.

14. The method of claim 8 further comprising providing one or more output signals to cause the output device to indicate absence of anxiety when the at least one extracted feature has a value within the predicted noise model.

* * * * *